United States Patent
Dvir et al.

(10) Patent No.: US 10,973,957 B2
(45) Date of Patent: Apr. 13, 2021

(54) PATTERNED ELECTROSPUN FIBERS FOR TISSUE ENGINEERING

(71) Applicant: Ramot at Tel-Aviv University Ltd., Tel-Aviv (IL)

(72) Inventors: Tal Dvir, LeHavim (IL); Sharon Fleischer, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 16/476,874

(22) PCT Filed: Jan. 10, 2018

(86) PCT No.: PCT/IL2018/050039
§ 371 (c)(1),
(2) Date: Jul. 10, 2019

(87) PCT Pub. No.: WO2018/131033
PCT Pub. Date: Jul. 19, 2018

(65) Prior Publication Data
US 2019/0336651 A1 Nov. 7, 2019

Related U.S. Application Data

(60) Provisional application No. 62/444,439, filed on Jan. 10, 2017.

(51) Int. Cl.
*A61L 27/56* (2006.01)
*A61K 38/38* (2006.01)
(Continued)

(52) U.S. Cl.
CPC ............. *A61L 27/56* (2013.01); *A61K 38/38* (2013.01); *A61L 27/227* (2013.01);
(Continued)

(58) Field of Classification Search
None
See application file for complete search history.

(56) References Cited

U.S. PATENT DOCUMENTS

2010/0129656 A1 5/2010 Zussman et al.
2011/0230411 A1 9/2011 Zussman et al.
(Continued)

FOREIGN PATENT DOCUMENTS

WO WO 2008/093342 8/2008
WO WO 2008/115160 9/2008
(Continued)

OTHER PUBLICATIONS

International Preliminary Report on Patentability dated Jul. 25, 2019 From the International Bureau of WIPO Re. Application No. PCT/IL2018/050039. (7 Pages).
(Continued)

*Primary Examiner* — Melissa S Mercier

(57) ABSTRACT

A composition of matter for tissue engineering is disclosed. The composition comprises a plurality of electrospun albumin fibers, wherein an outer surface of the composition comprises a pattern of ridges or indentations, wherein the ridges or indentations are wider than the diameter of a single electrospun albumin fiber of the plurality of electrospun albumin fibers.

8 Claims, 12 Drawing Sheets
(12 of 12 Drawing Sheet(s) Filed in Color)

(51) Int. Cl.
*A61L 27/22* (2006.01)
*A61L 27/54* (2006.01)
*A61L 31/04* (2006.01)
*A61L 27/38* (2006.01)
*C12N 5/00* (2006.01)

(52) U.S. Cl.
CPC ....... *A61L 27/3808* (2013.01); *A61L 27/3826* (2013.01); *A61L 27/3834* (2013.01); *A61L 27/54* (2013.01); *A61L 31/04* (2013.01); *C12N 5/0068* (2013.01); *A61L 2300/41* (2013.01); *A61L 2300/414* (2013.01); *A61L 2430/20* (2013.01); *C12N 2529/00* (2013.01); *C12N 2533/50* (2013.01); *C12N 2535/00* (2013.01)

(56) References Cited

U.S. PATENT DOCUMENTS

| | | | |
|---|---|---|---|
| 2013/0202669 | A1 | 8/2013 | Zussman et al. |
| 2014/0010850 | A1 | 1/2014 | Zussman et al. |
| 2016/0270729 | A1* | 9/2016 | Dvir .................... C12N 5/0068 |

FOREIGN PATENT DOCUMENTS

| | | |
|---|---|---|
| WO | WO 2013/151755 | 10/2013 |
| WO | WO 2013/172788 | 11/2013 |
| WO | WO 2014/186430 | 11/2014 |
| WO | WO2015071912 A1 * | 5/2015 ............... A61N 1/00 |
| WO | WO 2018/131033 | 7/2018 |

OTHER PUBLICATIONS

International Search Report and the Written Opinion dated Mar. 28, 2018 From the International Searching Authority Re. Application No. PCT/IL2018/050039. (11 Pages).

Fleischer et al. "Albumin Fiber Scaffolds for Engineering Functional Cardiac Tissues", Biotechnology and Bioengineering, 111(6): 1246-1257, Jun. 2014.

Lim et al. "Micropatterning and Characterization of Electrospun Poly (Epsilon-Caprolactone)/Gelatin Nanofiber Tissue Scaffolds by Femtosecond Laser Ablation for Tissue Engineering Applications", Biotechnology & Bioengineering, 108(1): 116-126, Published Online Sep. 1, 2010.

Nseir et al. "Biodegradable Scaffold Fabricated of Electrospun Albumin Fibers: Mechanical and Biological Characterization", Tissue Engineering: Part C, 19(4): 257-265, Published Online Jan. 16, 2013.

Supplementary European Search Report and the European Search Opinion dated Aug. 12, 2020 From the European Patent Office Re. Application No. 18738976.2. (8 Pages).

Zhao et al. "Recent Advances in Electrospun Nanofibrous Scaffolds for Cardiac Tissue Engineering", Advanced Functional Materials, XP055644188, 25(36): 5726-5738, Sep. 2015.

* cited by examiner

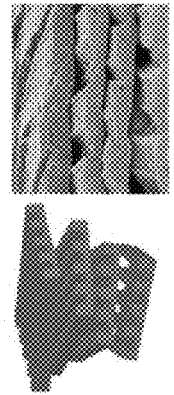
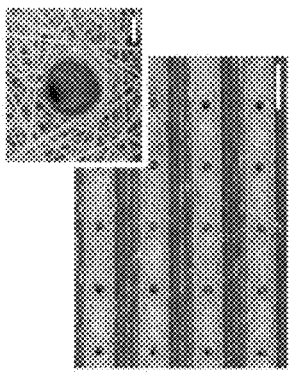
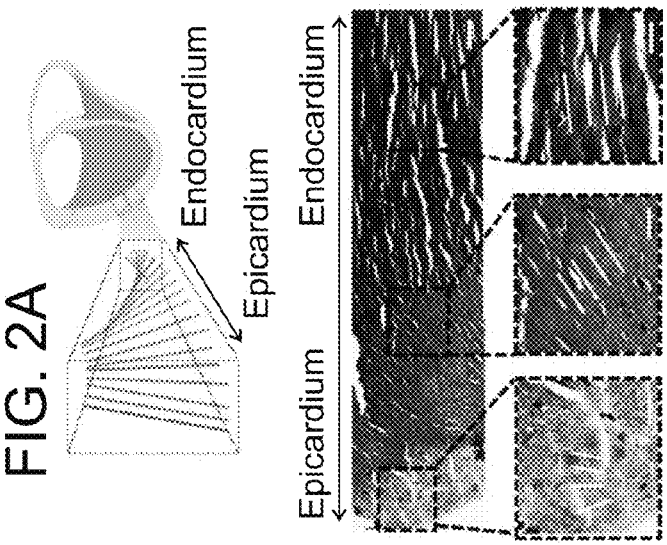
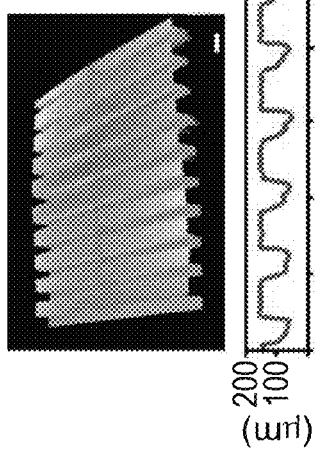
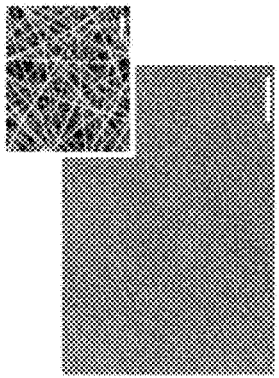
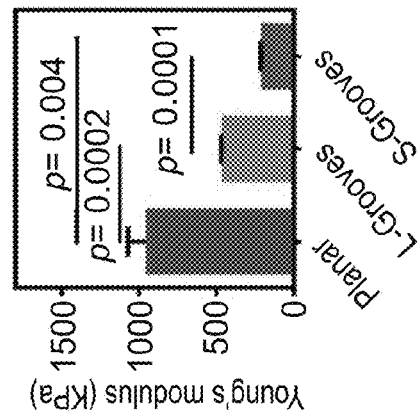
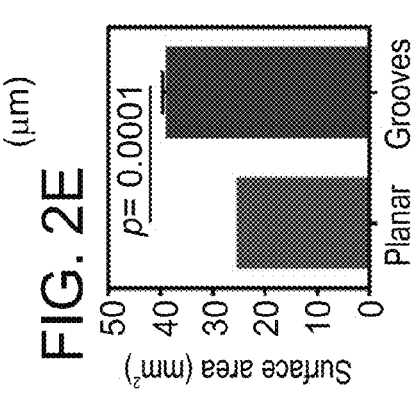
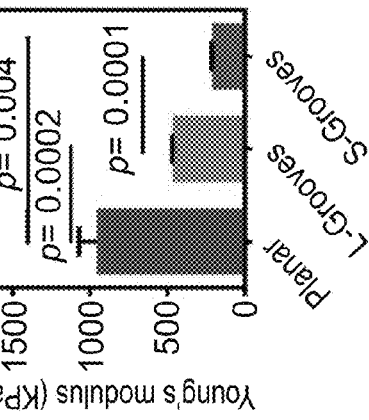
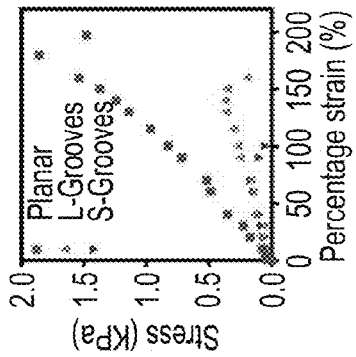

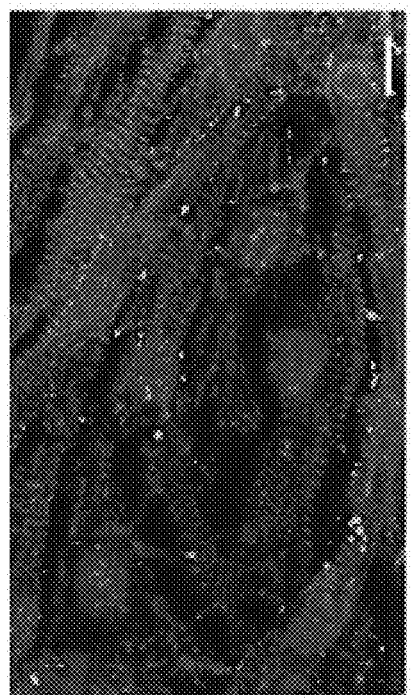
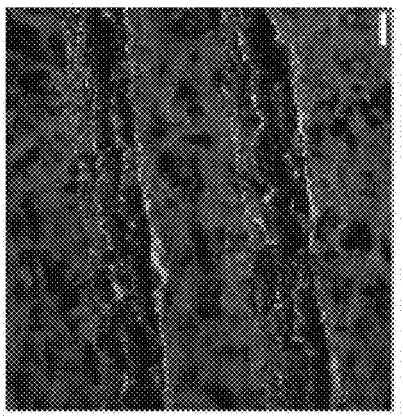
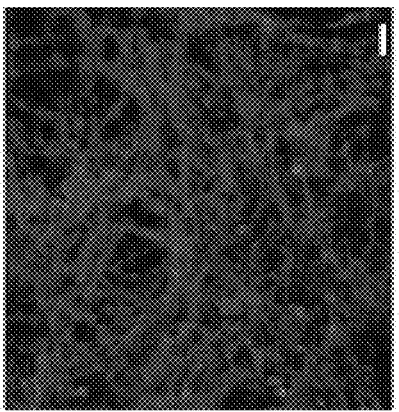
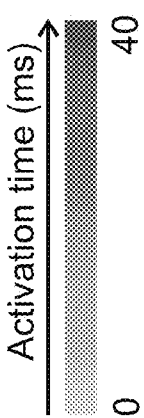
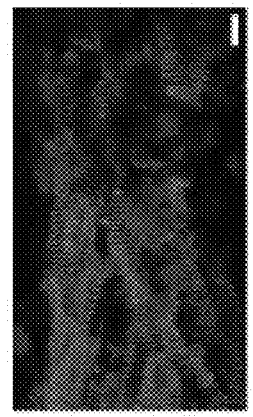
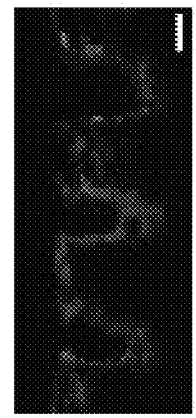
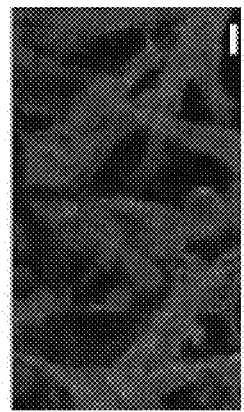
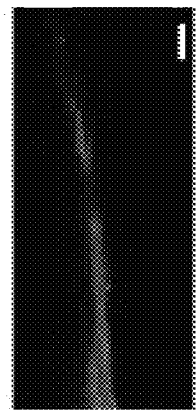

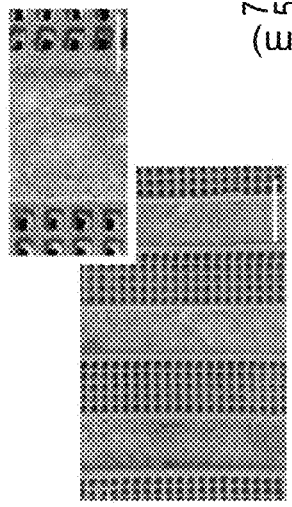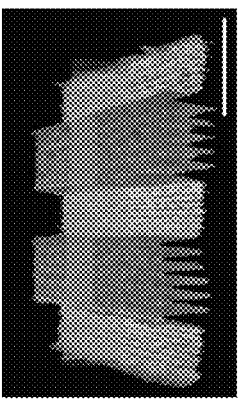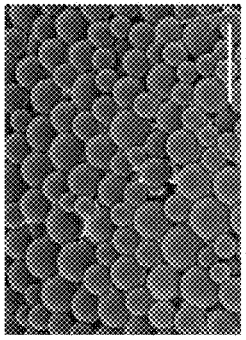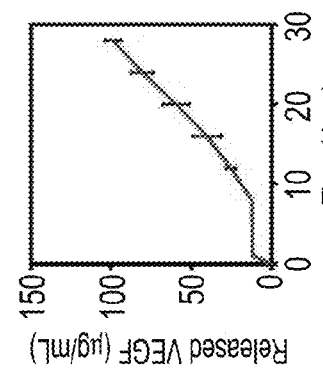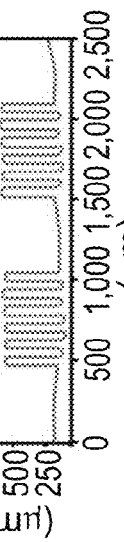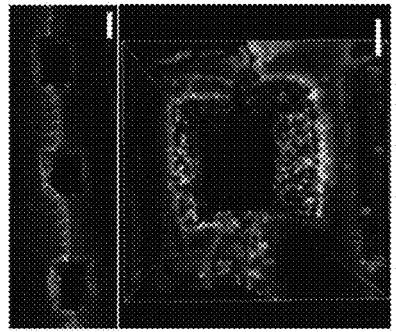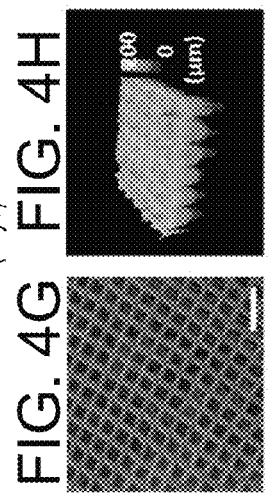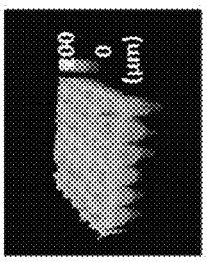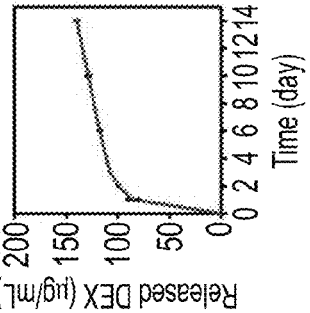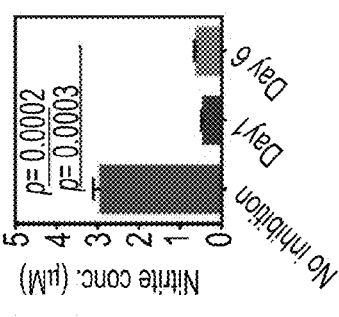

FIG. 10A
FIG. 10B
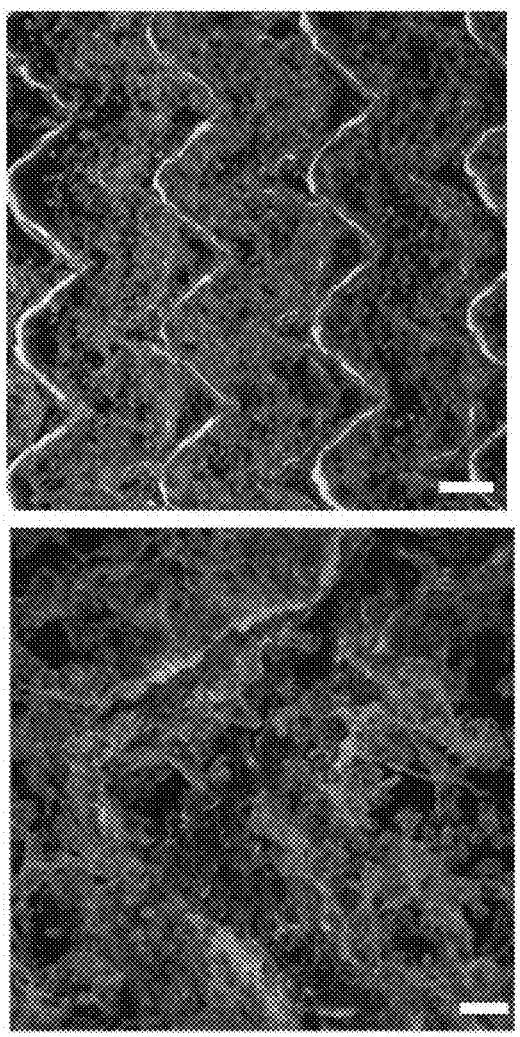
Activation time (ms)
0    20

PATTERNED ELECTROSPUN FIBERS FOR TISSUE ENGINEERING

RELATED APPLICATIONS

This application is a National Phase of PCT Patent Application No. PCT/IL2018/050039 having International filing date of Jan. 10, 2018, which claims the benefit of priority under 35 USC § 119(e) of U.S. Provisional Patent Application No. 62/444,439 filed on Jan. 10, 2017. The contents of the above applications are all incorporated by reference as if fully set forth herein in their entirety.

FIELD AND BACKGROUND OF THE INVENTION

The present invention, in some embodiments thereof, relates to scaffolds for tissue engineering and more specifically to patterned scaffolds comprising electrospun albumin fibers.

Cardiac tissue engineering aims to replace the damaged myocardium with a cardiac patch with structural and functional properties resembling the native tissue. The myocardium has a complex three-dimensional (3D) architecture, composed of a cellular component and an intricate fibrous network of the structural extracellular matrix (ECM). Each layer of these fibers guides cell organization to form anisotropic sheets of myocardial syncytia, responsible for directional contractions. To support the high metabolic demand of the contracting tissue, a dense vascular network in-between several cell layers provides oxygen and nutrients to the surrounding cells. Since heart muscle function is highly dependent on this unique structural organization, recapitulating both its anisotropic geometry throughout the ventricle wall and the internal vasculature is pivotal for engineering functional cardiac tissues for regenerative applications.

Numerous approaches have been used to recapitulate different structural properties of the heart. Technologies such as lithography and microfabrication enable a precise control over the biomaterial pattern and thus induce cell alignment and anisotropic electrical signal transfer. However, using these techniques for engineering thick 3D tissues with multi-cellular layers is still a challenge. Whilst macroporous scaffolds and hydrogels are suitable for engineering thick 3D tissues, different tissue layers within the scaffold cannot be separately controlled. Thus, the cells throughout the entire scaffolds are exposed to the same conditions and different tissue compartments cannot be engineered separately. For example, as cardiac cells and blood vessel cells require different culture medium and mature at different time points, engineering of spatially controlled vasculature within a cardiac patch may be a challenge. To overcome these challenges, recent advances in lithographic methods have enabled the layer-by-layer assembly of anisotropic 3D cardiac tissues and a vascular compartment embedded within. For example, Zhang and colleagues have reported on the production of a biodegradable scaffold with a built-in vasculature (21). In a different study by Ye and colleagues, the stacking of elastomeric micro-vessels and heart cell scaffolds to form 3D vascularized tissues was reported (20). However, the scaffolds used to create the layers do not recapitulate the fibrous nature of the cardiac ECM which is essential for tissue maturation.

Electrospinning is a well-established method used in tissue engineering to fabricate fibrous scaffolds. Fleisher et al teaches of the potential of albumin fiber scaffolds to promote the assembly of anisotropic and functional cardiac patches, however, their relatively low thickness (~100 µm) may limit their clinical applicability [Fleischer S, et al. (2014) Biotechnology and Bioengineering 111(6): 1246-1257].

Background art includes Lim et al., Biotechnol. Bioeng. 2011; 108: 116-126; Nseir et al., Tissue Engineering: Part C, Volume 19, Number 4, 2013, International Patent Application Number WO2008115160A1 and US Patent Application No. 20100129656.

SUMMARY OF THE INVENTION

According to an aspect of the present invention, there is provided a composition of matter for tissue engineering. The composition comprises a plurality of electrospun albumin fibers, wherein an outer surface of the composition comprises a pattern of ridges or indentations, wherein the width of an individual ridge or indentation of the pattern of ridges or indentations is wider than the diameter of a single electrospun albumin fiber of the plurality of electrospun albumin fibers.

According to an aspect of the present invention, there is provided a scaffold for tissue engineering comprising at least two layers, wherein each of the layers are fabricated from the composition of matter described herein, each layer comprising a pattern with distinct indentations or ridges.

According to an aspect of the present invention, there is provided a scaffold for tissue engineering comprising at least two layers, wherein each of the layers are fabricated from the composition of matter described herein, each of the at least two layers being seeded with cells of a different cell population.

According to an aspect of the present invention, there is provided a method of generating a composition of matter for tissue engineering comprising patterning an outer surface of a composition comprising a plurality of electrospun albumin fibers with indentations or ridges that are wider than the diameter of a single electrospun albumin fiber of the plurality of electrospun albumin fibers, thereby generating a composition of matter for tissue engineering.

According to an aspect of the present invention, there is provided a method of culturing cells comprising culturing the scaffold described herein under conditions that allow propagation of the cells, thereby culturing the cells.

According to embodiments of the present invention, the diameter of the plurality of electrospun albumin fibers is less than 10 µm.

According to embodiments of the present invention, the composition of matter is devoid of electrospun synthetic fibers.

According to embodiments of the present invention, the indentations form structures selected from the group consisting of grooves, holes and cages.

According to embodiments of the present invention, the indentations are grooves.

According to embodiments of the present invention, the width of the grooves is between 20 µm-500 µm.

According to embodiments of the present invention, the diameter of the holes is between 20 µm-500 µm.

According to embodiments of the present invention, the ridges of the grooves are patterned with holes.

According to embodiments of the present invention, the indentations do not form cages.

According to embodiments of the present invention, the structures are grooves and cages.

According to embodiments of the present invention, the composition of matter further comprises a cell population seeded on the outer surface.

According to embodiments of the present invention, the cell population comprises a single cell type.

According to embodiments of the present invention, the cell population comprises cells selected from the group consisting of cardiomyocytes, endothelial cell, pancreatic beta cells, hepatocytes, skin cells, lung cells and skeletal muscle cells.

According to embodiments of the present invention, the cell population comprises stem cells.

According to embodiments of the present invention, the composition of matter further comprises cardiomyocytes seeded on the outer surface.

According to embodiments of the present invention, the composition of matter further comprises endothelial cells seeded on the outer surface.

According to embodiments of the present invention, the structures comprise cages.

According to embodiments of the present invention, the cages are loaded with particles comprising an agent selected from the group consisting of a growth promoting agent, a neurotransmitter, a differentiating agent, a pro-angiogenic agent, an anti-inflammatory agent and a drug.

According to embodiments of the present invention, at least one of the layers is seeded with cells.

According to embodiments of the present invention, the cell population comprises cells selected from the group consisting of cardiomyocytes, endothelial cell, pancreatic beta cells, hepatocytes, skin cells, lung cells and skeletal muscle cells.

According to embodiments of the present invention, the first of the at least two layers is seeded with cardiomyocytes and the second of the at least two layers is seeded with endothelial cells.

According to embodiments of the present invention, the first layer comprises a pattern of grooves.

According to embodiments of the present invention, the second layer comprises a pattern of grooves and cages.

According to embodiments of the present invention, the cages are loaded with particles comprising an agent selected from the group consisting of a growth promoting agent, a differentiating agent, a neurotransmitter, a pro-angiogenic agent, an anti-inflammatory agent and a drug.

According to embodiments of the present invention, the scaffold comprises at least three layers, wherein the third layer is patterned with cages loaded with particles comprising an agent selected from the group consisting of a growth promoting agent, a neurotransmitter, a differentiating agent, a pro-angiogenic agent, an anti-inflammatory agent and a drug.

According to embodiments of the present invention, the at least two layers are adhered to one another using a biological glue.

According to embodiments of the present invention, the patterning is effected using a laser.

According to embodiments of the present invention, the method further comprises seeding the composition of matter with a cell population.

According to embodiments of the present invention, the indentations form a pattern selected from the group consisting of grooves, holes and cages.

According to embodiments of the present invention, the indentations form cages.

According to embodiments of the present invention, the method further comprises loading the cages with particles comprising an agent selected from the group consisting of a growth-promoting agent, a neurotransmitter, a differentiating agent, a pro-angiogenic agent, an anti-inflammatory agent and a drug.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 illustrates the schematics of the bottom-up approach to assemble a functional cardiac patch.

Figure 1:
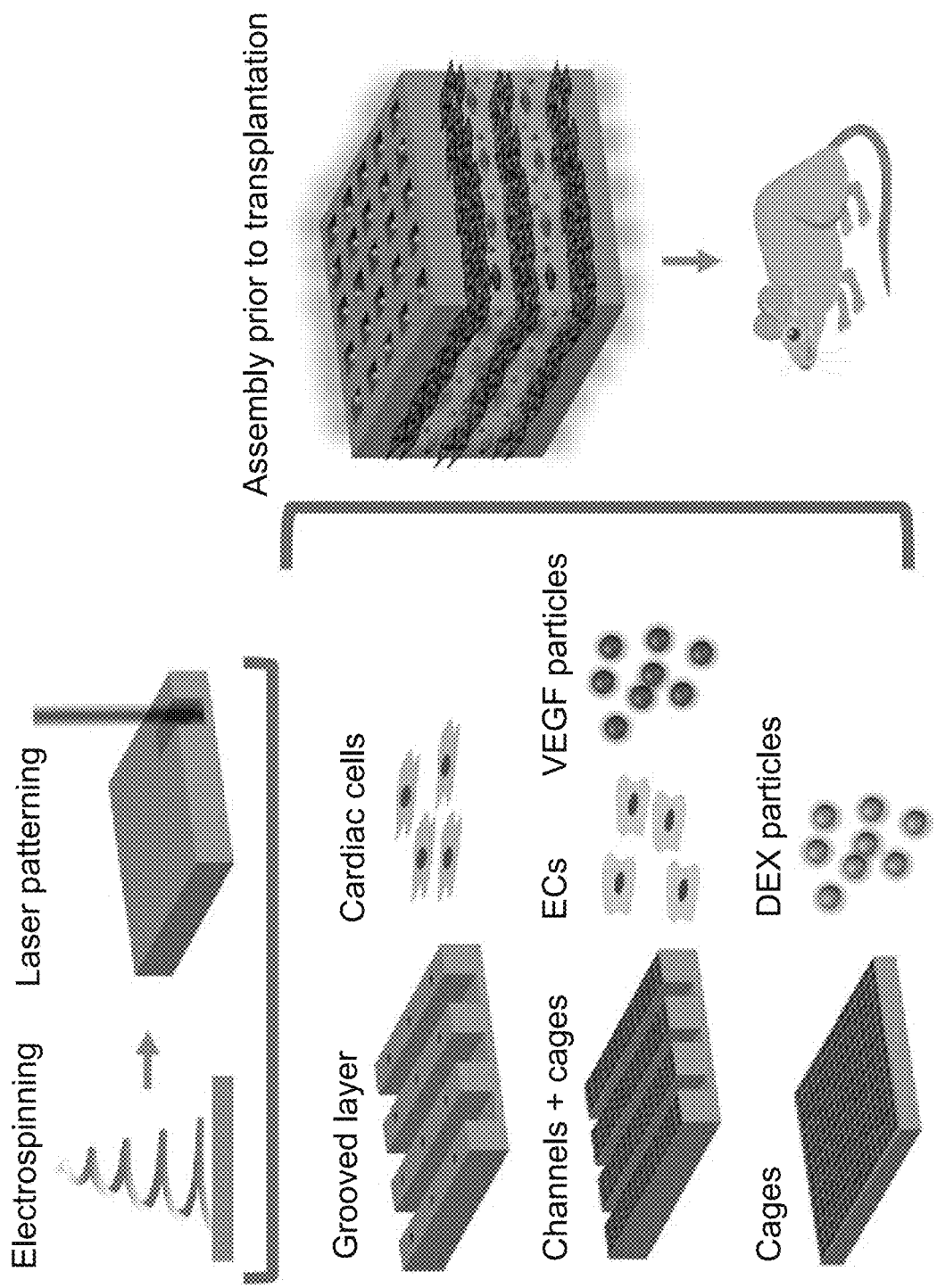

FIGS. 2A, 2B, 2C, 2D, 2E, 2F, 2G and 2H illustrate the biomimetic design and fabrication of electrospun fiber scaffolds according to embodiments of the present invention. (A) Schematics and Masson's trichrome staining of a transmural block, cut from the ventricular wall, showing the macroscopic variation in fiber orientation across the wall. (B,C) SEM micrographs of planar electrospun scaffolds (B, scale bars: 200 µm and 20 µm in the inset) and grooved electrospun scaffolds with microholes (C, scale bars: 200 µm and 20 µm in the inset). (D) Confocal image of grooved electrospun scaffolds (scale bar: 100 µm), and topography analysis. (E) Surface area. (F) Schematics and SEM micrographs of grooved electrospun scaffolds stacked with a slight angle shift. (G) Representative stress-strain curves. (H) Young's modulus. The results represent mean values ±SEM. (n≥5 in each group). Statistical evaluations were performed by unpaired Student's t tests.

FIGS. 3A, 3B, 3C, 3D and 3E are images illustrating cardiac tissue organization and function. (A,B) Immunofluorescence images of α-sarcomeric actinin (in pink, cell nuclei are shown in blue) of cardiomyocytes cultured within planar (A, Scale bars: 50 µm, 20 µm, and 50 µm) and grooved scaffolds (B, Scale bars: 50 µm, 20 µm, and 50 µm). Lower panels show side views of the tissue constructs. (C) Connexin 43 molecules (green) are found between adjacent cells, indicating on their electrical coupling (Scale bar: 10 µm). (D,E) Heat maps showing randomly oriented electrical signal propagation of an engineered cardiac tissues within the planar scaffolds (D, scale bar: 500 µm) and anisotropic propagation within the grooved scaffolds (E, scale bar: 500 µm).

FIGS. 4A, 4B, 4C, 4D, 4E, 4F, 4G, 4H, 4I, 4J and 4K illustrate fabrication of a predefined vascular layer and sustained release system layers according to embodiments of the present invention. (A) SEM micrographs of micro-patterned tunnels and in-between cage-like structures (scale bars: 500 μm and 200 μm in the inset). (B) Confocal image of the micro-tunnels (scale bars: 500 μm) and a topography analysis. (C) SEM micrographs of PLGA micro-particles (scale bar: 100 μm). (D) Cumulative release of VEGF. (E) SEM micrographs of PLGA micro-particles deposited within the cage-like structures adjacent to the micro-tunnels (scale bar: 100 μm) (F) Immunofluorescent images of CD31 (green, cell nuclei are shown in blue) of endothelial cells cultured within the micro-tunnels to form lumens (scale bars: top: 200 μm and bottom: 100 μm). (G,H) SEM (G, scale bar: 200 μm) and confocal (H) micrographs of micro-patterned cage-like structures. (I) SEM micrographs of PLGA particles deposited on cage-like structures (scale bar: 50 μm). (J) Cumulative release of DEX. (K) Anti-inflammatory activity of DEX released from PLGA micro-particles as indicated by inhibition of NO secretion (measured as nitrite, a stable metabolite of NO) from activated macrophages. The results represent mean values ±SEM. (n≥5 in each group). Statistical evaluations were performed by unpaired Student's t tests.

FIGS. 5A, 5B, 5C, 5D, 5E, 5F, 5G, 5H, 5I, 5J, 5K, 5L, 5M and 5N illustrate in-vitro assembly and in-vivo vascularization of 3D multifunctional patch. (A) Schematics of assembled scaffolds (blue) integrated by thin layers of glue (pink). (B,C) Micrographs of two layers integrated by ECM glue and visualized by SEM (B, arrow heads indicate on the presence of the glue, scale bar: 50 μm) and Masson's trichrome staining (collagen stained in blue, scaffolds stained in red, scale bar: 50 μm). (D) Adhesion strength. (E) Assembled layers forming a 5 mm thick tissue. (F) Quantification of calcium transients (as quantified through normalized fluorescence intensity) without stimulation or with 1 and 2 Hz stimulation, stimulation pattern can be seen in the lower part of the figure. (G-I) Vascularization of the patch without (G) and with (H) VEGF-releasing particles, 2 weeks after subcutaneous transplantation in rats. (I) cross sectioning of the explanted patch. (J) H&E staining of thin sections of the explanted patch (scale bar: 100 μm). (K) Infiltration of a host blood vessel containing red blood cells (white arrow) into the engineered construct (black arrow; scale bar: 100 μm). (L) Mature blood vessels populated the tissue construct with the sustained VEGF release as judged by the stained smooth muscle cells (pink—SMA, blue—cell nuclei, scale bar: 50 μm). Blood vessel density (M) and the area in % (N) occupied by the blood vessels. The results represent mean values ±SEM. (n≥3 in each group). Statistical evaluations were performed by unpaired Student's t tests.

Figure 6:
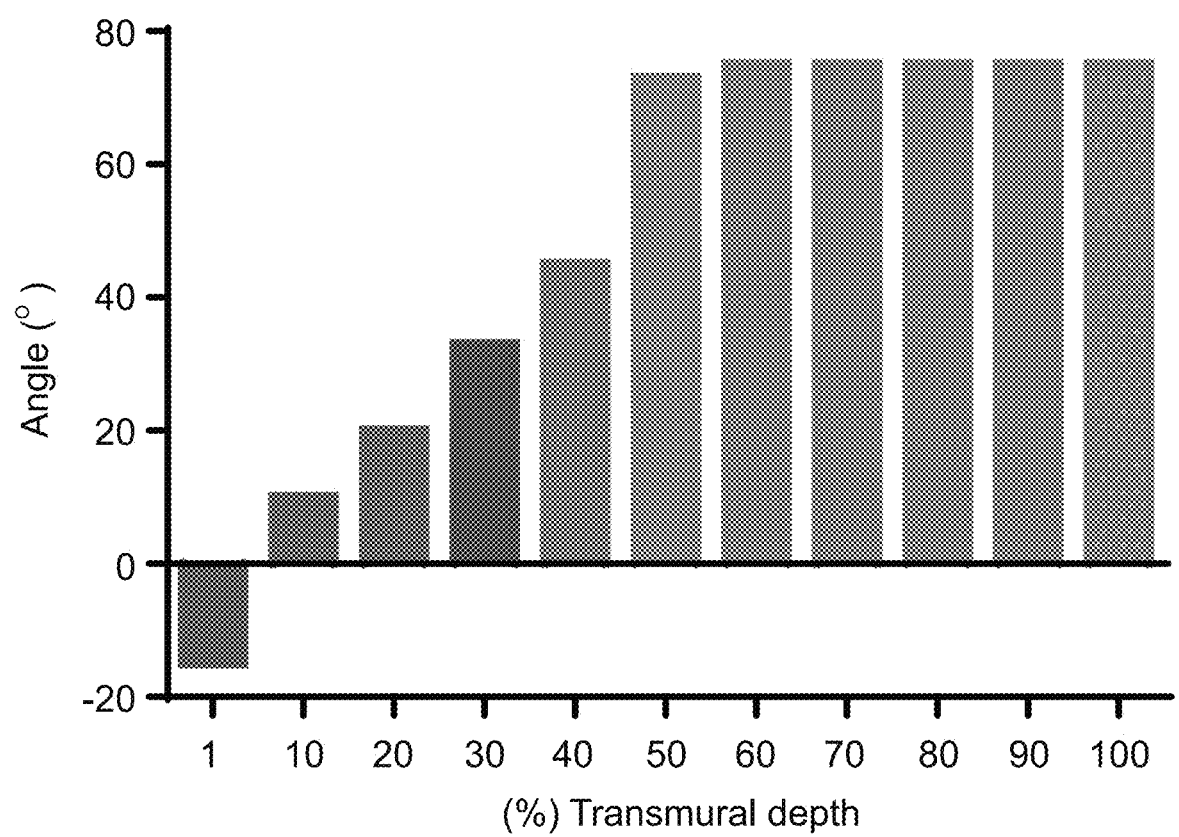

FIG. 6 illustrates quantification of collagen fiber orientation throughout the LV wall.

Figure 7A:
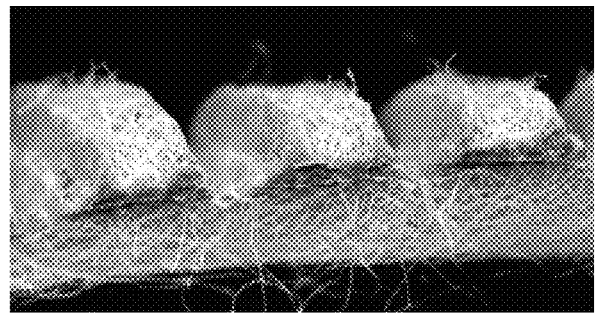
Figure 7B:
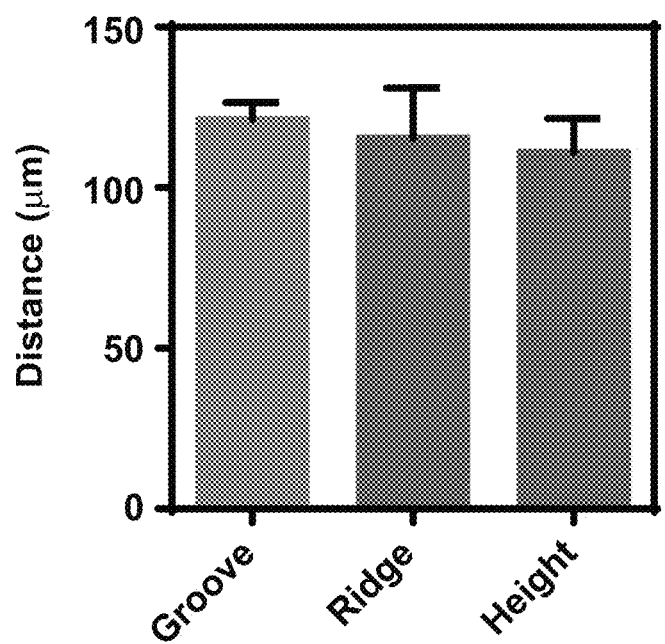

FIGS. 7A and 7B illustrate properties of micro-grooved scaffolds, according to embodiments of the present invention. (A) SEM micrograph of cross section of the scaffold (scale bar: 200 μm). (B) Analysis of groove and ridge width and depth.

Figure 8A:
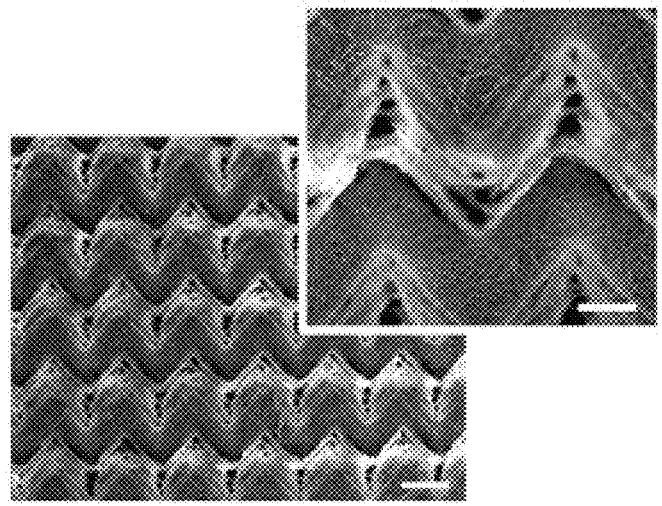
Figure 8B:
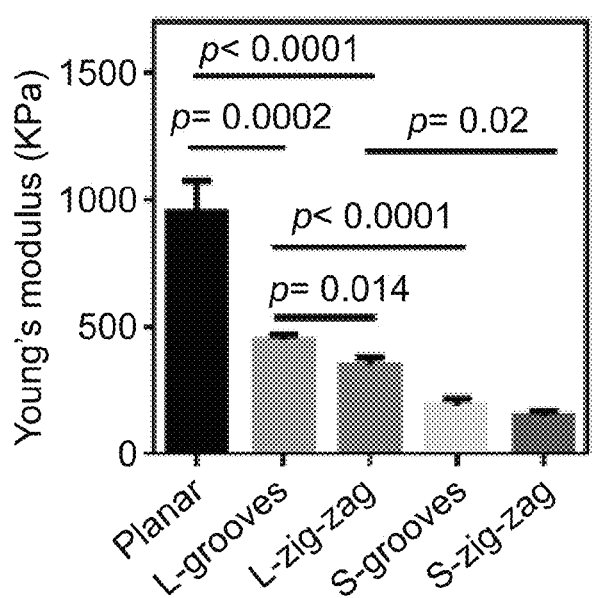
Figure 8C:
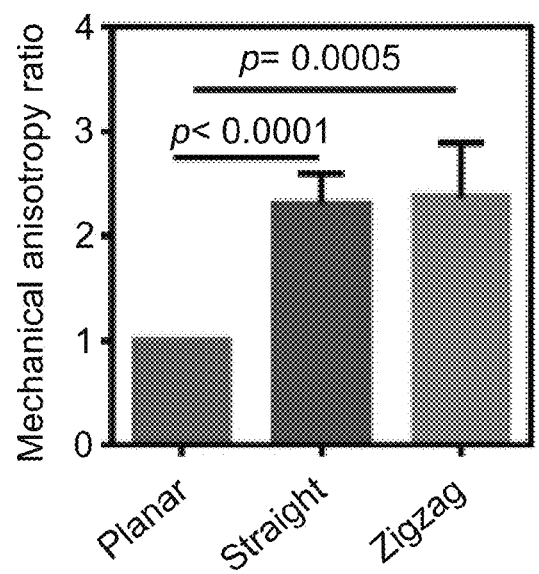

FIGS. 8A, 8B and 8C illustrate properties of micro-patterned zigzag grooves according to embodiments of the present invention. (A) SEM micrographs (scale bar: 250 μm and 100 μm). (B) Young's modulus. (C) Anisotropy ratio.

Figures 9A, 9B:
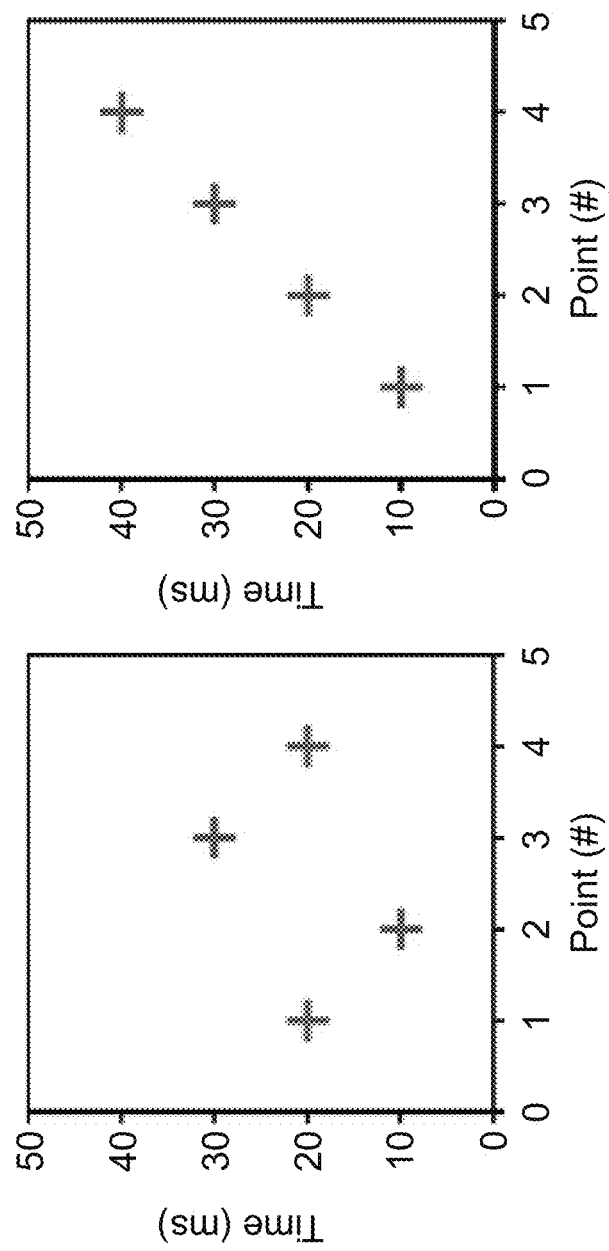

FIGS. 9A and 9B illustrate results of the analysis of electrical signal propagation on randomly chosen points on the planar (A) and micro-grooved scaffolds (B).

FIGS. 10A and 10B illustrate cardiac tissue organization on zigzag micro-grooved scaffolds according to embodiments of the present invention. (A) Immunofluorescent images of α-sarcomeric actinin (in pink) of cardiomyocytes cultured in zigzag grooves (scale bars: 100 μm and 20 μm). (B) heat maps showing electrical signal propagation in a single zigzag groove (scale bar: 200 μm).

FIGS. 11A, 11B, 11C, 11D, 11E and 11F illustrate layer assembly and integration according to embodiments of the present invention. (A) Images showing adhesion of several tissue layers, revealing that in 90° parallel to the ground the layers did not separate from one another. (B, C) immunofluorescent images of a single tissue layer (B, scale bar: 20 μm) and three integrated layers (C, scale bar: 100 μm) stained for α-sarcomeric actinin (in pink) of cardiomyocytes and collagen (in green) comprising the ECM glue (cell nuclei are stained blue). (D,E) SEM micrographs of (D) two layers of vasculature, glued on top of each other to form closed lumens, and incorporated in-between two cardiac tissue layers (scale bar: 200 μm), (E) cross section of the DEX layer. (F) H&E staining of cross section of the DEX layer, 2 weeks after transplantation, showing the presence of a PLGA micro-particle (in yellow, scale bar: 50 μm).

Figure 12A:
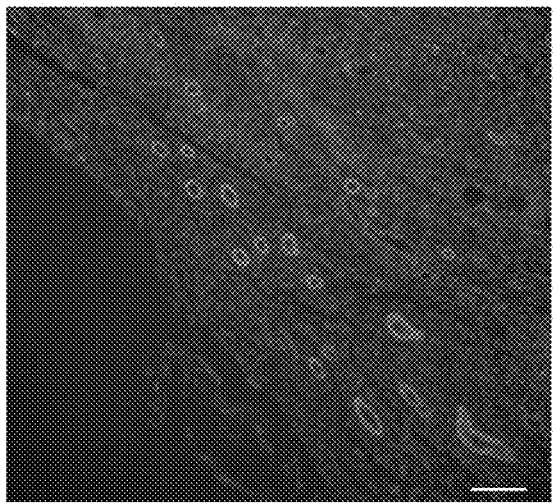
Figure 12B:
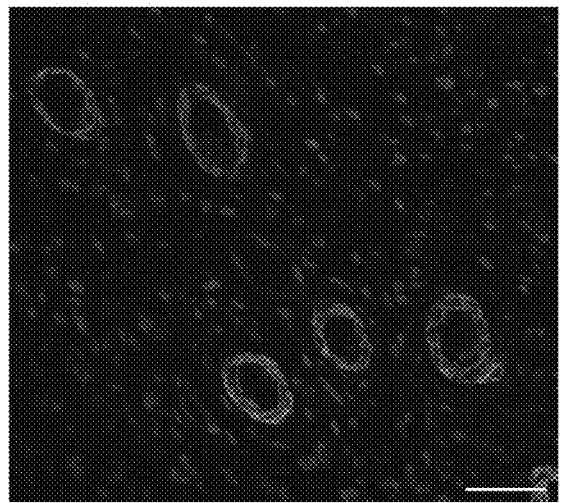

FIGS. 12A and 12B illustrate that mature blood vessels populated the tissue construct with the sustained VEGF release system as judged by anti-SMA immunofluorescence (pink, cell nuclei are shown in blue, scale bar: 50 μm and 100 μm.

DESCRIPTION OF SPECIFIC EMBODIMENTS OF THE INVENTION

The present invention, in some embodiments thereof, relates to scaffolds for tissue engineering and more specifically to patterned scaffolds comprising electrospun albumin fibers.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have devised a platform for assembling a modular thick cardiac patch, containing layers of cardiac tissue, blood vessels, pro-angiogenic and anti-inflammatory factors. The 3D structural complexity of the fibrous ECM was recapitulated by the assembly of micro-patterned electrospun layers, mimicking the variation in collagen alignment throughout the left ventricular (LV) wall. The present inventors have shown that these layers mimicked both the stiffness and mechanical anisotropy of the heart muscle, and therefore may improve the potential of a cardiac patch to properly integrate into the heart muscle. Cardiac cells cultured within these layers assembled into aligned and elongated cardiac bundles, resembling the natural tissue morphology.

Whilst further reducing the present invention to practice, the present inventors engineered pre-defined vasculature with sufficient distance from the cardiac tissue to enable the diffusion of oxygen and nutrients. This platform enabled a simple scalable production of mm-thick tissues by simply placing them one on top of the other and gluing them with an ECM-based biological glue. Compared to other tissue-engineering approaches, such as 3D printing or using macroporous scaffolds, since this method enables the engineering of individual layers, each layer can be cultured under its optimal conditions prior to assembly. Microparticulate systems for prolonged release of growth factors or small molecules can be easily incorporated into the patch and manipulate the engineered tissue or the host according to the physiological needs. Although the present data supports the engineering of a vascularized cardiac patch, the present inventors conceive that different structures can be patterned on electrospun fibers to provide support to other tissues that are comprised of defined layers, including but not limited to the liver and lung.

Thus, according to one aspect of the present invention there is provided a composition of matter for tissue engineering, comprising a plurality of electrospun albumin fibers, wherein an outer surface of the composition comprises a pattern of ridges or indentations, wherein the width of an individual ridge or indentation of said pattern of ridges or indentations is wider than the diameter of a single electrospun albumin fiber of said plurality of electrospun albumin fibers.

The term "tissue engineering" refers to the process of generating tissues ex-vivo for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

In one embodiment, the composition of matter is for cardiac tissue engineering.

The term "cardiac tissue" as used herein refers to a population of cells that together are able to function to fulfill at least one functional phenotype specific to cardiac tissue (e.g. appropriate response to a chronotropic agent and/or ability to spontaneously contract in a synchronized function). The cardiac tissue is typically a mammalian cardiac tissue and more preferably a human cardiac tissue.

In another embodiment, the composition of matter is for hepatic tissue engineering, pancreatic tissue engineering, skin tissue engineering, lung tissue engineering or skeletal muscle engineering.

In one embodiment, the composition of matter comprises a scaffold.

As used herein, the term "scaffold" refers to a three dimensional matrix upon which cells may be ex vivo cultured (i.e., survive and preferably proliferate for a predetermined time period).

Typically, the scaffolds of the present invention are porous. The porosity of the scaffold may be controlled by a variety of techniques known to those skilled in the art. The minimum pore size and degree of porosity is dictated by the need to provide enough room for the cells and for nutrients to filter through the scaffold to the cells. The maximum pore size and porosity is limited by the ability of the scaffold to maintain its mechanical stability after seeding.

According to a preferred embodiment of this aspect of the present invention, the scaffold has an average pore size of about 50-5000 $\mu m^2$. The diameter of the fibers may be between 0.005-10 $\mu m$ or between 50 nm-5 $\mu m$. The Young's modulus of the fibers is typically between 1-10,000 KPa, with the percentage strain being between 10-10,000%.

As used herein, the term "electrospinning" refers to a process that uses an electric field to draw a solution comprising albumin from the tip of the capillary to a collector. A high voltage DC current is applied to the solution which causes a jet of the solution to be drawn towards the grounded collector screen. Once ejected out of the capillary orifice, the charged solution jet gets evaporated to form fibers and the fibers get collected on the collector. The size and morphology of the fibers thus obtained depends on a variety of factors such as viscosity of the solution, molecular weight, nature of the polymer or ceramic and other parameters regarding the electrospinning apparatus. The electrospinning process to form polymer nanofibers has been demonstrated using a variety of polymers [Huang, et al. Composites Science and Technology 2003; 63]. According to this aspect of the present invention, the electrospun fibers are albumin fibers (e.g. Albumin fraction V). Electrostatic spinning is a process by which polymer fibers of nanometer to micrometer size in diameters and lengths up to several kilometers can be produced using an electrostatically driven jet of polymer solution or polymer melt. The polymer solution or melt may comprise one or more therapeutically active molecules at concentrations determined by the ordinary skilled artisan.

The term "fibre" as used herein, refers to a unit of matter characterized by a high ratio of length-to-width.

The term "albumin" refers to a family of globular proteins, which includes the serum albumins. Albumins are naturally found in blood plasma and may or may not be glycosylated.

The albumin may be derived from any animal species, for example human, bovine, porcine, monkey, or rodent. Alternatively, the albumin may be chemically synthesized (i.e. recombinant).

The human serum protein is a 65-70 kDa protein, and the sequence is known in the art (see Accession No. NM 000477) or UnitProt P02868. Recombinant production of HA (rHA) in microorganisms has been disclosed in EP 330 451 and EP 361 991. Animal homologs are known in the art.

In order to generate electrospun albumin fibers, albumin is first dissolved in a dissolving agent. Such agents include 2,2,2-trifluoroethanol (TFA), acetone, methylene chloride or chloroform. The dissolved albumin is then typically denatured using a denaturing agent such as β-mercaptoethanol (β-ME). In one embodiment, the only protein in the dope is albumin.

In another embodiment, the dope is devoid of a synthetic polymer.

Electrospinning of the dope albumin solution may be conducted under room temperature, using a syringe pump (e.g. Harvard Apparatus), a 14-32 gauge needle—e.g. 23-gauge needle (inner diameter between 0.1-2 mm, e.g. 0.37 mm), under a voltage supply of 5-50 kV (e.g. 12 kV). The solution may be delivered at a rate between 0.1-5 ml/h, e.g. 2 ml/per hour.

Typically, mats of albumin fibers are collected having a size between 0.5-5 $\mu m$ in diameter.

It will be appreciated that once electrospun, the polymerized albumin mats may be cut into any size or shape depending on their subsequent use. Exemplary sizes are between about 1-500 mm in length and/or width.

Following electrospinning, the albumin scaffolds may then be patterned.

Patterning may be effected using a femtosecond laser so as to pattern various topographies and geometries such as grooves, posts, pits cage-like structures, honeycomb and other quadrangles. The size scales of the topographies ranges from the nano scale to the micro scale.

According to a preferred embodiment, the width of the pattern (grooves, ridges, holes etc.) on the surface of the scaffold/composition is greater than 10 $\mu m$—for example between 10-500 $\mu m$, or between 10-200 $\mu m$. Typically, the width of one structure of the pattern (i.e. groove, ridge, hole diameter, etc.) is greater than the diameter of one of the electrospun fibers.

The present inventors have shown that patterning of the aforementioned topographies preserves the fibrous nature of the scaffolds.

The patterning may increase the surface area by 1.5-100 fold or greater.

The present invention contemplates scaffolds comprising individual electrospun layers, wherein the number of adhesion/contact points, the relative orientation of the surface topographical features, size and geometry of the features, dimensions of each layer and number of layers can be adjusted during the manufacturing process according to the specific necessities of the target tissue. If a layer of tissue with each layer having a different organization and cell is required than multilayers of different orientations can be separately prepared and then brought together to create a construct with a multilayer, multiorientation structure. If an enhanced level of interaction is necessary between the different cell types present, or if an increased permeability for transference of solutes, growth factors, bioactive agents is needed, layers can be rendered partially porous by addition of appropriate solute particles of desired dimensions and their subsequent dissolution by a proper solvent which only dissolves these particles and not the film material. Similar property may be achieved by pore formation upon exposure to particulates and electromagnetic radiation.

In one embodiment, the scaffold comprises two layers. In another embodiment, the scaffold comprises three layers. In another embodiment, the scaffold comprises four layers. In still another embodiment, the scaffold comprises five layers. In still another embodiment, the scaffold comprises six layers. In one embodiment, the scaffold comprises seven layers. In another embodiment, the scaffold comprises eight layers. In another embodiment, the scaffold comprises nine layers. In still another embodiment, the scaffold comprises 10 layers. In still another embodiment, the scaffold comprises 11 layers. In one embodiment, the scaffold comprises 12 layers. In another embodiment, the scaffold comprises 13 layers. In another embodiment, the scaffold comprises 14 layers. In still another embodiment, the scaffold comprises 15 layers. In still another embodiment, the scaffold comprises 16 layers.

It will be appreciated that the number of layers, the order with which they are stacked and the type of patterning will depend on the type of tissue being generated.

Thus, according to a particular embodiment, at least one of the layers in the scaffold comprises grooves. In another embodiment, at least one of the layers in the scaffold comprises cages. In still another embodiment, at least one of the layers in the scaffold comprises both grooves and cages. According to yet another embodiment, the scaffold comprises a first layer of grooves, a second layer of channels and cages and a third layer of cages see for example FIG. 1.

The cages may be loaded with biological agents directly or via particles, whereby the particles are at least partially biodegradable. The cages and particles are both selected to be of a particular size such that the particles are not able to traverse the "bars" of the cages prior to biodegradation. Upon biodegradation of the particles, the agents incorporated within diffuse out of the cages and onto the cells seeded on the scaffold. A variety of agents, including, but not limited to a growth promoting agent, a neurotransmitter, a differentiating agent, a pro-angiogenic agent, an anti-inflammatory agent and a drug, all of which are described herein below may be incorporated into the cages. The agents themselves are "caged", such that they are released slowly, over time (e.g. up to 10 mg over 150 days) into the cells seeded on the scaffold.

The particles, which are loaded into the cages, are typically made of biodegradable polymers, including both naturally occurring biodegradable polymers and synthetic biodegradable polymers.

The phrase "biodegradable polymer" as used herein, refers to a polymer or polymers which degrade in vivo, and wherein erosion of the polymer or polymers occurs over time. The terms "biodegradable" and "bioerodible" are equivalent and are used interchangeably herein.

Such bioerodible or biodegradable materials may be used to fabricate temporary structures. In exemplary embodiments, biodegradable or bioerodible materials may be biocompatible. Examples of biocompatible biodegradable polymers which are useful to generate the particles of this embodiment of the present invention include, but are not limited to, polylactic acid, polyglycolic acid, polycaprolactone, and copolymers thereof, polyesters such as polyglycolides, polyanhydrides, polyacrylates, polyalkyl cyanoacrylates such as n-butyl cyanoacrylate and isopropyl cyanoacrylate, polyacrylamides, polyorthoesters, polyphosphazenes, polypeptides, polyurethanes, polystyrenes, polystyrene sulfonic acid, polystyrene carboxylic acid, polyalkylene oxides, alginates, agaroses, dextrins, dextrans, polyanhydrides, biopolymers such as collagens and elastin, alginates, chitosans, glycosaminoglycans, and mixtures of such polymers. In still other embodiments, a mixture of non-biodegradable and bioerodible and/or biodegradable scaffold materials may be used to form a biomimetic structure of which part is permanent and part is temporary.

Individual layers could be adhered to one another using a variety of biological glues while maintaining cell viability.

Typically, the force needed to separate the glued layers should be greater than the force needed to separate non-glued layers. More importantly, the binding force between the glued layers should be strong enough to withstand manual manipulation and surgical suturing to the host. In one embodiment, the integrated layers are cultured for a further amount of time after gluing prior to transplantation into the host so as to strengthen their adherence. Preferably, the adhesion strength of the biological glue is between 1 mN-10 N.

According to a particular embodiment, the biological glue is a fibrin glue, a cyanoacrylate polymerizable adhesive, a gelatin based or a thermoresponsive ECM-based hydrogel which solidifies at 37° C., an example of which is disclosed in U.S. patent application Ser. No. 15/702,834, the contents of which are incorporated herein by reference.

Exemplary agents that may be incorporated into the scaffold (e.g. in the cages thereof, attached to the scaffold, impregnated therein) of the present invention include, but are not limited to those that promote cell adhesion (e.g. fibronectin, integrins), cell colonization, cell proliferation, cell differentiation, cell extravasation and/or cell migration. Thus, for example, the agent may be an amino acid, a small molecule chemical, a peptide, a polypeptide, a protein, a DNA, an RNA, a lipid and/or a proteoglycan.

Proteins that may be incorporated into the scaffolds of the present invention include, but are not limited to extracellular matrix proteins, cell adhesion proteins, growth factors, cytokines, hormones, proteases and protease substrates. Thus, exemplary proteins include vascular endothelial-derived growth factor (VEGF), activin-A, retinoic acid, epidermal growth factor, bone morphogenetic protein, TGFβ, hepatocyte growth factor, platelet-derived growth factor, TGFα, IGF-I and II, hematopoetic growth factors, heparin binding growth factor, peptide growth factors, erythropoietin, interleukins, tumor necrosis factors, interferons, colony stimulating factors, basic and acidic fibroblast growth factors, nerve growth factor (NGF) or muscle morphogenic factor (MMP). The particular growth factor employed should be appropriate to the desired cell activity. The regulatory effects of a large family of growth factors are well known to those skilled in the art.

Drugs that may be incorporated into the scaffold (either directly or in particles placed in the cages) include immunosuppressive agents.

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

Typically, the layers of the scaffold are seeded individually, such that each layer is seeded with a compatible cell type. Thus, for example for generating cardiac tissue, cardiac cells may be used to seed a grooved layer and endothelial cells may be used to seed a channeled layer, wherein the channeled layer also comprises cages which comprise agents that promote angiogenesis—e.g. VEGF.

Seeding of the cells on the scaffolds is a critical step in the establishment of the engineered tissue of the present invention. Since it has been observed that the initial distribution of cells within the scaffold after seeding is related to the cell densities subsequently achieved, methods of cell seeding require careful consideration. Thus, cells can be seeded in a scaffold by static loading, or, more preferably, by seeding in stirred flask bioreactors (scaffold is typically suspended from a solid support), in a rotating wall vessel, or using direct perfusion of the cells in medium in a bioreactor. Highest cell density throughout the scaffold is achieved by the latter (direct perfusion) technique. An exemplary seeding procedure is described in the Materials and Methods section herein below.

The cells may be seeded directly onto the scaffold, or alternatively, the cells may be mixed with a gel which is then absorbed onto the interior and exterior surfaces of the scaffold and which may fill some of the pores of the scaffold. Capillary forces will retain the gel on the scaffold before hardening, or the gel may be allowed to harden on the scaffold to become more self-supporting. Alternatively, the cells may be combined with a cell support substrate in the form of a gel optionally including extracellular matrix components. An exemplary gel is Matrigel™, from Becton-Dickinson. Matrigel™ is a solubilized basement membrane matrix extracted from the EHS mouse tumor (Kleinman, H. K., et al., Biochem. 25:312, 1986). The primary components of the matrix are laminin, collagen I, entactin, and heparan sulfate proteoglycan (perlecan) (Vukicevic, S., et al., Exp. Cell Res. 202:1, 1992). Matrigel™ also contains growth factors, matrix metalloproteinases (MMPs [collagenases]), and other proteinases (plasminogen activators [PAs]) (Mackay, A. R., et al., BioTechniques 15:1048, 1993). The matrix also includes several undefined compounds (Kleinman, H. K., et al., Biochem. 25:312, 1986; McGuire, P. G. and Seeds, N. W., J. Cell. Biochem. 40:215, 1989), but it does not contain any detectable levels of tissue inhibitors of metalloproteinases (TIMPs) (Mackay, A. R., et al., BioTechniques 15:1048, 1993). Alternatively, the gel may be growth-factor reduced Matrigel, produced by removing most of the growth factors from the gel (see Taub, et al., Proc. Natl. Acad. Sci. USA (1990); 87 (10:4002-6). In another embodiment, the gel may be a collagen I gel, alginate, or agar. Such a gel may also include other extracellular matrix components, such as glycosaminoglycans, fibrin, fibronectin, proteoglycans, and glycoproteins. The gel may also include basement membrane components such as collagen IV and laminin. Enzymes such as proteinases and collagenases may be added to the gel, as may cell response modifiers such as growth factors and chemotactic agents.

The cells that are seeded on the scaffolds of the present invention may be derived from any organism including for example mammalian cells, (e.g. human), plant cells, algae cells, fungal cells (e.g. yeast cells), prokaryotic cells (e.g. bacterial cells).

According to a particular embodiment, the cells are preferably intact (i.e. whole), and preferably viable, although it will be appreciated that pre-treatment of cells, such as generation of cell extracts or non-intact cells are also contemplated by the present invention.

The cells may be fresh, or have undergone freezing another preservation in any other way known in the art (e.g. cryopreserved).

Examples of cells that may be seeded onto the scaffolds to generate cardiac tissue include but are not limited to cardiomyocytes, endothelial cells and fibroblasts.

Other examples of cells that may be used to fabricate the scaffolds of the present invention include stem cells (pluripotent stem cells, multipotent stem cells or tissue-specific stem cells). According to another embodiment, the cells are ex-vivo terminally differentiated or partially differentiated from stem cells.

As used herein, the term "cardiomyocytes" refers to fully or at least partially differentiated cardiomyocytes. Thus, cardiomyocytes may be derived from stem cells (such as embryonic stem cells or adult stem cells, such as mesenchymal stem cells). Methods of differentiating stem cells along a cardiac lineage are well known in the art—[Muller-Ehmsen J, et al., Circulation. 2002; 105:1720-6; Zhang M, et al., J Mol Cell Cardiol. 2001; 33:907-21, Xu et al, Circ Res. 2002; 91:501-508, and U.S. Pat. Appl. No. 20050037489, the contents of which are incorporated by reference herein]. According to one embodiment the stem cells are derived from human stem cell lines, such as H9.2 (Amit, M. et al., 2000. Dev Biol. 227:271).

According to one embodiment the cardiomyocytes of the present invention are at least capable of spontaneous contraction. According to another embodiment, the cardiomyocytes of the present invention express at least one marker (more preferably at least two markers and even more preferably at least three markers) of early-immature cardiomyocytes (e.g. atrial natriuretic factor (ANF), Nk×2.5, MEF2C and α-skeletal actin). According to another embodiment, the cardiomyocytes of the present invention express at least one marker (more preferably at least two markers and even more preferably at least three markers) of fully differentiated cardiomyocytes (e.g. MLC-2V, α-MHC, α-cardiac actin and Troponin I).

Screening of partially differentiated cardiomyocytes may be performed by a method enabling detection of at least one characteristic associated with a cardiac phenotype, as described hereinbelow, for example via detection of cardiac specific mechanical contraction, detection of cardiac specific structures, detection of cardiac specific proteins, detection of cardiac specific RNAs, detection of cardiac specific electrical activity, and detection of cardiac specific changes in the intracellular concentration of a physiological ion.

According to a particular embodiment, at least one scaffold layer is seeded with endothelial cells.

Endothelial cells may be human embryonic stem cell (hESC)-derived endothelial cells (Levenberg, et al., Proc Natl Acad Sci USA (2002) 99, 4391-4396, the contents of which are incorporated by reference herein), or primary endothelial cells cultured from e.g. human umbilical vein (HUVEC), or biopsy-derived endothelial cells such as from the aorta or umbilical artery. The endothelial cells of the present invention may also be derived from humans (either autologous or non-autologous) e.g. from the blood or bone marrow. In addition the endothelial cells may be derived from other mammals, for example, humans, mice or cows. For example, endothelial cells may be retrieved from bovine aortic tissue. Typically, the endothelial cells are isolated from a tissue from where they are derived.

In one embodiment, human embryonic endothelial cells are produced by culturing human embryonic stem cells in the absence of LIF and bFGF to stimulate formation of embryonic bodies, and isolating PECAM1 positive cells from the population. HUVEC may be isolated from tissue according to methods known to those skilled in the art or purchased from cell culture laboratories such as Cambrex Biosciences or Cell Essentials.

In another embodiment, at least one scaffold layer is seeded with fibroblast cells (e.g. mouse embryonic fibroblasts or human embryonic fibroblasts). Fibroblasts may be isolated from tissue according to methods known to those skilled in the art (e.g. obtained from E-13 ICR embryos) or purchased from cell culture laboratories such as Cambrex Biosciences or Cell Essentials.

Typically, the layers are initially cultured separately as each cell type in each layer requires different culturing conditions (e.g. different length of time, different medium). Thus, for example cardiac layers of 5-10 days may be fabricated with endothelial cell layers of 2-5 days. An exemplary medium for culturing cardiac cells is M199 medium and an exemplary medium for culturing endothelial cells is EGM 2 supplemented with growth factors, such as VEGF. Once placed together, the entire construct may be cultured in EGM2 or M199.

It will be appreciated that culturing conditions are selected which allow for the cells to propagate. When a single cell type is cultured on a scaffold layer, optimal culturing conditions may be used for that cell type. When the scaffold is comprised of more than one layer of different cell types, the culturing conditions may be adapted such that both cell types are capable of propagating, even though the conditions may be more optimal for one cell type than the other.

Thus, according to another aspect of the present invention there is provided a method of treating cardiac disorder associated with a defective or absent myocardium in a subject, the method comprising transplanting a therapeutically effective amount of the compositions of the present invention into the subject, thereby treating the cardiac disorder.

The method may be applied to repair cardiac tissue in a human subject having a cardiac disorder so as to thereby treat the disorder. The method can also be applied to repair cardiac tissue susceptible to be associated with future onset or development of a cardiac disorder so as to thereby inhibit such onset or development.

The present invention can be advantageously used to treat disorders associated with, for example, necrotic, apoptotic, damaged, dysfunctional or morphologically abnormal myocardium. Such disorders include, but are not limited to, ischemic heart disease, cardiac infarction, rheumatic heart disease, endocarditis, autoimmune cardiac disease, valvular heart disease, congenital heart disorders, cardiac rhythm disorders, impaired myocardial conductivity and cardiac insufficiency. Since the majority of cardiac diseases involve necrotic, apoptotic, damaged, dysfunctional or morphologically abnormal myocardium, and since the vascularized cardiac tissue of the present invention displays a highly differentiated, highly functional, and proliferating cardiomyocytic phenotype, the method of repairing cardiac tissue of the present invention can be used to treat the majority of instances of cardiac disorders.

According to one embodiment, the method according to this aspect of the present invention can be advantageously used to efficiently reverse, inhibit or prevent cardiac damage caused by ischemia resulting from myocardial infarction.

According to another embodiment, the method according to this aspect of the present invention can be used to treat cardiac disorders characterized by abnormal cardiac rhythm, such as, for example, cardiac arrhythmia.

As used herein the phrase "cardiac arrhythmia" refers to any variation from the normal rhythm of the heart-beat, including, but not limited to, sinus arrhythmia, premature heat, heart block, atrial fibrillation, atrial flutter, pulsus alternans and paroxysmal tachycardia.

According to another embodiment, the method according to this aspect of the present invention can be used to treat impaired cardiac function resulting from tissue loss or dysfunction that occur at critical sites in the electrical conduction system of the heart, that may lead to inefficient rhythm initiation or impulse conduction resulting in abnormalities in heart rate.

The method according to this aspect of the present invention is effected by transplanting the composition of the present invention to the appropriate site (e.g. heart) of the subject. As used herein, "transplanting" refers to the placement of a biocompatible substrate, such as the scaffold described herein, into a subject in need thereof, with or without prior seeding and/or infiltration of cells.

The mode used for delivery of the compositions of the invention to the defective site e.g. myocardium may be critical in establishing tissue regeneration in vivo. Standard delivery to myocardial sites can be used for injectable, fluidized, emulsified, gelled, or otherwise semi-fluid materials, such as direct injecting (e.g. with a needle and syringe), or injecting with a percutaneous catheter. For materials that have been rendered wholly or partially vaporized, force-driven delivery of the material can be used, for example, $CO_2$ powering emission of fine emulsion, micronizing an injectable solution, ink jet delivery, spray with a conventional atomizer or spray unit, or other type of vaporized delivery. Some of these vaporized formulations can be delivered using a percutaneous catheter adapted for delivery of a vaporized formulation.

For materials that are essentially solid, such as the scaffolds described herein, physically depositing the material will be the most prudent mode of delivery. For example a patch, sponge, strip, weave, or other geometrically defined material form should be placed at the site of deposit either during surgery, or with a percutaneous minimally invasive catheter capable of depositing all or portions of solid material at the site. Preferred modes of delivery will be minimally invasive delivery procedures, which reduce the risk of infection and provide an easier recovery for the patient.

In all cases, before a mode is used to treat a patient, the feasibility and effectiveness of any one delivery mode or combination of modes can be tested in a test mammal prior to actual use in humans.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Masson's trichrome staining: Adult rat hearts were cryofixed and sectioned into 10 µm slices. The sections were stained with Masson's trichrome (Bio-Optica, Milano, Italy) for cell and collagen detection Electrospinning-Albumin fiber scaffolds: Bovine serum albumin [BSA; Fraction V, MP Biomedicals, Aurora, Ohio; 10% and 14% (w/v)] was dissolved in TFE and distilled water (9:1, respectively), followed by addition of excess β-mercaptoethanol (Merck, Darmstadt, Germany) for overnight reaction. The solution was electrospun at room temperature, using a syringe pump (Harvard Apparatus) delivered at a rate of 2 mL/h. A high voltage supply (Glassman High Voltage, NJ, US) was used to apply a 12 kV potential between the capillary tip and the grounded aluminum collector placed at a distance of 14 cm.

Micro-patterning: A femto-second laser (Master femto, ELAS) was used for the micropatterning of albumin fiber scaffolds (1,026 nm, 1-5 W. 150 Hz)

Fabrication of Microfluidic Networks via Inner Ablation: A nanosecond laser system was used for the fabrication of inicrofluidic networks in hydrogels: a PALM MicroBearn system (1 ns pulses, 100 Hz frequency, 355 nm) from Carl Zeiss Microscopy (Gottingen, Germany) set with a 10× objective (NA=0.25) and a constant stage speed. 95 µm s$^{-1}$, was used in all experiments.

Scaffold 3D imaging and topographical analysis. Confocal images of the micro-patterned scaffolds were taken using an Olympus LEXT 4000 confocal microscope SEM: Samples were mounted onto aluminum stubs with conductive paint and sputter-coated with an ultrathin (150 Å) layer of gold in a Polaron E 5100 coating apparatus (Quorum technologies, Laughton, UK). The samples were viewed under JCM-6000PLUS NeoScope Benchtop (JEOL USA Inc., Peabody, Ma.).

Mechanical Properties:

Albumin fiber scaffolds. Scaffolds were cut into a rectangular shape (gauge length: 20 mm, and width: 4 mm) and tested using a Lloyd tensile testing instrument (model LS1) with a 20 N load cell at a rate of 5 mm min$^{-1}$.

ECM glue integration. Scaffolds were cut into a rectangular shape (gauge length: 20 mm, and width: 4 mm). Following, a 10 µL drop of ECM glue was placed on the short edge of one rectangular scaffold, and a second scaffold was placed on top of the drop forming a congruent area of 4 mm×4 mm between the two scaffolds. Later, the scaffolds were incubated for 30 min and then tested using a Lloyd tensile testing instrument (model LS1) with a 5 N load cell at a rate of 3 mm min$^{-1}$.

Cardiac cell isolation, seeding and cultivation: Cardiac cells were isolated according to Tel Aviv University ethical use protocols. Briefly, left ventricles of 0-3-day-old neonatal Sprague-Dawley rats (Envigo Laboratories, Israel) were harvested, and cells were isolated using six cycles (30 min each at 37° C.) of enzyme digestion with collagenase type II (95 U/mL; Worthington, Lakewood, N.J.) and pancreatin (0.6 mg/mL; Sigma-Aldrich) in Dulbecco's modified Eagle Medium (DMEM, $CaCl_2.2H_2O$ (1.8 mM), KCl (5.36 mM), $MgSO_4.7H_2O$ (0.81 mM), NaCl (0.1 M), $NaHCO_3$ (0.44 mM), $NaH_2PO_4$ (0.9 mM)). After each round of digestion cells were centrifuged (600 G, 5 min) and resuspended in culture medium composed of M-199 supplemented with 0.6 mM $CuSO_4 5.H_2O$, 0.5 mM $ZnSO_4.7H_2O$, 1.5 mM vitamin B12, 500 U/mL Penicillin and 100 mg/mL streptomycin, and 0.5% (v/v) FBS. To enrich the cardiomyocytes population, cells were suspended in culture medium with 5% FBS and pre-plated twice (45 min). Cell number and viability were determined by a hemocytometer and trypan blue exclusion assay. Two million cardiac cells were seeded onto the devices by adding 15 µL of the suspended cells followed by a 45 min incubation period (Humidified incubator, 37° C., 5% $CO_2$). Following, cell constructs were supplemented with culture medium (5% FBS) and further incubated.

Immunostaining: Cell constructs were fixed and permeabilized in 100% cold methanol for 10 min, washed three times in DMEM-based buffer and then blocked for 1 h at room temperature in DMEM-based buffer containing 2% FBS, after which the samples were washed three times. Cardiac tissues were incubated with primary mouse anti α-sarcomeric actinin antibody (1:750, Sigma-Aldrich), washed three times and incubated for 1 h with Alexa Fluor 647 conjugated goat anti-mouse antibody (1:500; Jackson, West Grove, Pa.). HUVECs were stained for CD31 (1:100, Abcam), washed three times and incubated for 1 h with Alexa Fluor 488 conjugated goat anti-rabbit antibody (1:500; Jackson). For nuclei detection, the cells were incubated for 3 min with Hoechst 33258 (1:100; Sigma) and washed three times. Samples were visualized using a scanning laser confocal microscope (Nikon Eclipse Ni).

Calcium imaging: Constructs were incubated with 10 µM fluo-4 AM (Invitrogen, Waltham, Mass.) and 0.1% Pluronic F-127 (Sigma-Aldrich) for 45 minutes at 37° C. Constructs were then washed in medium and imaged using an inverted fluorescent microscope (Nikon Eclipse TI). Videos were acquired with a digital CMOS camera Orcaflash 4.0 (Hamamatsu, Japan) at 100 frames/sec using NIS element software. Electrical signal propagation was measured by ImageJ (NIH).

PLGA particles. PLGA particles loaded with VEGF: These particles were prepared using the solid-in-oil-in-oil emulsion solvent evaporation technique. Briefly, 150 mg of PLGA (75% Av. Mw 7000-17,000, acid terminated and 25% Av. Mw 30,000-60,000, Sigma-Aldrich) were dissolved in 750 µL acetonitrile. Next, 7.5 µg VEGF (Peprotech) were dissolved in 112 µL double distilled deionized water, 15 µL 20% (w/v) aqueous BSA solution, 22.5 µl 7% (w/v) aqueous sucrose solution and stirred. Following, 600 µL of acetonitrile solution were added in increments of 150 µl and stirred for 2 minutes. This solution was then added to a 15 mL solution of acetonitrile, stirred for 2 min and centrifuged (10 min, 4,500 rpm). Next, the precipitate was washed twice with acetonitrile. The remaining acetonitrile was removed and the precipitate was suspended in the PLGA solution, stirred for 5 min and sonicated for 1 min. This solution was then added to a 75 mL light mineral oil with 2% Span-80 (Sigma-Aldrich) and stirred at 600 rpm under reduced pressure overnight. The following day, the micro-particles were washed three times with isopropanol, dried under reduced pressure and suspended in 2% (v/v) BSA solution in PBS. To measure VEGF release from the particles, they were suspended in microcentrifuge tubes containing PBS solution with 0.1% BSA and incubated at 37° C. under continues rotation at 15 rpm. VEGF concentration was determined using a human VEGF ELISA kit (Peprotech).

PLGA particles loaded with DEX: An oil-in-water emulsion solvent extraction/evaporation technique was used. One hundred mg of PLGA (Av. Mw 30,000-60,000, Sigma- Aldrich) were dissolved in 400 µL of methylene chloride, and 10 mg of dexamethasone was dispersed in this solution and stirred for 1 h. This organic phase was added to 2 mL of a 1% (w/v) aqueous PVA (Mw 25,000) solution and stirred for 3 min at 800 rpm. Following, the emulsion was added to 30 mL of a 0.1% (w/v) aqueous PVA solution and stirred under reduced pressure for 3 h at 25° C. The resulting microspheres were washed three times with double distilled deionized sterile water. To measure DEX release from the particles, they were suspended in a PBS solution with 0.1% BSA and microcentrifuge tubes were rotated at 15 rpm at 37° C. The amount of released DEX was quantified by absorbance at 242 nm (a characteristic band of DEX) using a NanoDrop ND-1000 UV-Vis Spectrophotometer.

The Effect of released dexamethasone on Nitric oxide production in macrophages: RAW 264.7 cells (American Type Culture Collection (ATCC)) were cultured at 37° C. in a humidified, 5% carbon dioxide atmosphere in Dulbecco's modified Eagle medium (without phenol red) supplemented with 10% heat-inactivated fetal bovine serum, penicillin (100 units/ml), streptomycin (100 µg/ml) and L-glutamine (2 mM) (Biological Industries, Israel). $3.25 \times 10^4$ RAW 264.7 cells in a total volume of 60 µl were seeded per well in 96 well plate. Twenty-four hours later, the cells were supplemented with additional 20 µl medium without or with the released dexamethasoneon sampled at day 1 and day 6. Following 24 hours, 20 µl of growth media containing 25 ng/ml of IFN gamma (PeproTech) were added to each well, reaching a final concentration of 5 ng/ml. After 24 h incubation, 50 µl samples of cell growth medium were analyzed for nitrite concentration (used as an indicator of NO production) using Griess reagent (Promega). Cell viability was determined by Thiazolyl Blue Tetrazolium Bromide (MTT) assay (n≥5 in each group).

Assessment of electrical signal transfer between the stacked layers: Two gold electrodes (300 nm) were evaporated onto the bottom albumin layer with a 1 cm distance between them. Cells were seeded between the electrodes to form the bottom layer of the tissue. Pristine cardiac layers were glued onto the bottom layer to allow the cells to migrate and create cell-cell interactions in the z axis. After 7 days of incubation, calcium imaging was performed to the top layer. The constructs were then washed in medium and the top layer was imaged using a fluorescence microscope (Nikon Eclipse TI). Movies were acquired with a Hamamatsu Orcaflash 4.0 (Hamamatsu) at 100 frames/s.

In-vivo implantation and histology: Recipient SD male rats (150-200 g, Envigo Laboratories, Israel) were anesthetized using a combination of Ketamine (40 mg/kg) and Xylazine (10 mg/kg) according to Tel Aviv University ethical use protocols. Subcutaneous implantation of samples was performed by creating a small incision to the back. Scaffolds were inserted into the cavity created by the incision. Two weeks after transplantation the rats were sacrificed and the samples were extracted. Following samples were dehydrated in graduated ethanol steps (70-100%), fixed in formalin and paraffin embedded. Five µm thick sections were prepared using a microtome. Sections were stained with hematoxylin and eosin. Samples were visualized using an inverted fluorescence microscope (Nikon Eclipse TI). For immunofluorescence, sections were rehydrated (100-0%) and then antigen retrieval was performed in citrate buffer. Following, sections were stained with primary rabbit anti-SMA (1:100, Abcam) and Alexa Fluor 647 conjugated goat anti-rabbit antibody (1:500; Jackson) and visualized using a scanning laser confocal microscope (Nikon Eclipse Ni).

Statistical analysis: Statistical analysis data are presented as means±SEM. Differences between samples were assessed by a Student's t-test. All analyses were performed using GraphPad Prism version 6.00 for Windows (GraphPad Software). $p<0.05$ was considered significant.

Results

Tissues in the body are comprised of different cellular and extracellular layers. The myocardium is composed of anisotropic layers of cells and collagen fibers with varying orientations across its transmural depth (5, 6). To explore the variations in transmural orientation in detail, adult rat hearts were harvested, sliced and stained for cells and collagens (FIG. 2A). Analysis of collagen fiber orientation revealed that the degree of alignment from the epicardial side to the endocardial side had a 100° shift (FIG. 6). Currently, the only technique to assemble a shift in cell alignment is by assembling several tissue layers atop each other. To address this challenge, thin layers of fibrous scaffolds were fabricated by electrospinning of albumin (FIG. 2B). To increase the surface area of the fibrous scaffold and mimic native anisotropy of the natural ECM, micro-grooves were patterned onto the scaffold by a femto-second laser (FIGS. 2C and 7A). To increase the mass transfer through the different layers, micro-holes (d=40±0.8 µm) were created on the ridges of each layer (FIG. 2C). Such holes were previously shown to promote efficient exchange of nutrients and oxygen (21). The pattern dimensions were measured using a scanning laser confocal microscopy, resulting in groove width of 115±5 µm, ridge width of 120±2 µm and height of 110±10 µm (FIGS. 2D and 7B). The patterned grooves significantly increased the surface area of the scaffolds from 25 mm$^2$ to 39±0.9 mm$^2$ ($p=0.0001$ (FIG. 2E). Stacking several of these grooved scaffolds with a slight angle shift (FIG. 2G) may promote the essential circular contraction.

For proper integration with the healthy part of the heart, the mechanical properties of the patch should have similar characteristics. The Young's modulus of the human heart ranges between 200 to 500 kPa in the contracted state (25-27). Moreover, the left ventricle (LV) has unique mechanical anisotropy, with a measured anisotropy ratio of 2.1, which is essential for proper function (7). FIG. 2G shows the representative stress-strain behavior of the different scaffolds. Further analysis of these results revealed that while the Young's modulus of the planar layers was 950±125 KPa, the micro-grooved scaffolds had significantly lower Young's modulus of 450±20 KPa in the long-axis of the grooves and 95±25 KPa in the short axis (FIG. 2H; $p=0.0002$ and $p=0.004$, respectively). The anisotropy ratio of the grooved scaffolds was 2.3, indicating their resemblance to the anisotropic LV and their potential for engineering cardiac patches that generate a strong contraction force. The mechanical properties and anisotropy can be further controlled by patterning different structures (FIGS. 8A-C).

Next, the present inventors sought to evaluate the potential of the grooved fibrous layers to promote anisotropic cardiac tissue assembly. Cardiac cells were isolated from the ventricles of neonatal rats and cultured for 7 days. Sarcomeric α-actinin immunostaining revealed that the cells cultured on the non-patterned albumin fiber scaffolds assembled into a randomly oriented tissue (FIG. 3A). On the other hand, in the grooved-scaffolds the cells acquired the micro-pattern and assembled into aligned cardiac cell bundles, as in their natural microenvironment (FIG. 3B). Higher magnification images of the tissues revealed cell elongation and massive striation in both scaffolds. However, only the cells on the grooved scaffolds exhibited oriented striation (FIG. 3B). Side view images revealed that contrary to the planar scaffolds, in the patterned scaffolds cardiomyocytes were able to adhere to the walls of the grooves and thus formed thicker 3D structures (FIGS. 3A and 3B), with high expression of connexin 43 proteins, which are associated with electrical coupling between adjacent cells (FIG. 3C). As tissue structure is usually translated to function, an analysis of the electrical signal propagation was performed by calcium imaging. Heat maps show that while the electrical signal generated by the tissues cultured within the planar scaffolds propagated randomly (FIG. 3D), the cells in the patterned scaffolds transferred the signal in the direction of the grooves (FIG. 3E and FIGS. 10A-B). Analysis of electrical signal propagation on randomly chosen points on the planar or the patterned scaffolds or the grooved, revealed directional propagation only in the grooved scaffold (FIGS. 9A-B).

One of the major challenges that jeopardizes the clinical translation of engineered tissues is the inability to form and maintain thick viable tissues (28, 29). Three-dimensional engineered tissues require an efficient and constant supply of oxygen and nutrients for cell growth and function. In-vitro, in the absence of a vascular network, perfusion bioreactors are used for mass transfer to the core of the tissue (30, 31). However, once the tissues are transplanted, the lack of proper vasculature jeopardizes the success of the treatment (32). One of the strategies for engineering prevascularized cardiac tissues is the co-culture of cardiac cells with blood vessel-forming cells such as endothelial cells (33, 34). However, both cell types require distinct conditions, including culture medium, growth factors, ECM topography and composition and cultivation time. The present inventors have designed a platform which allows separate growth, maturation and organization of the endothelial cells and then integration with the cardiac compartment. Micro-tunnels with dimensions of 450 μm were patterned to form a pre-defined vasculature (FIGS. 4A and 4B). Cage-like structures were designed in-between the tunnels to accommodate controlled release systems to continuously supply signals for vascularization. Next, double emulsion PLGA microparticles (FIG. 4C), enabling a long-term release of VEGF (FIG. 4D) were deposited into the cages (FIG. 4E). Such a release profile of VEGF has been shown to improve the vascularization of an engineered tissue and encourage anastomosis in-vivo, contributing to better engraftment after transplantation (35, 36). The micro-tunnels were then seeded with endothelial cells to form large closed lumens (FIG. 4F). VEGF release from the engineered blood vessels may further encourage sprouting of endothelial cells and formation of new capillaries in-between the pre-cultured vessels (36). Furthermore, the particles can be more accurately inserted into the cages using a micro-injector, and can even be loaded with other growth factors or cytokines, such as PDGF or SDF-1 to attract other blood vessel-forming cells, or IGF-1 for cardioprotection (37).

Another challenge in tissue engineering is the host response to the transplanted tissue. An acute inflammatory response against the engineered patch could profoundly limit the success of its integration and thereby jeopardize the regeneration process (38). Therefore, a second microparticulate layer to release an anti-inflammatory drug from the patch's outskirts to its surroundings. Cage-like structures were patterned (FIGS. 4G and 4H) and PLGA microparticles containing dexamethasone (DEX) were scattered on top (FIG. 4I). This anti-inflammatory layer was able to release the drug for at least 14 days (FIG. 4J) and attenuated the activation of macrophages, as measured by their nitric oxide secretion (FIG. 4K). Although this layer was designed to affect the patch's surroundings by decreasing the immune response after transplantation, other small molecules can be loaded into the particles to affect the engineered tissue as well. For example, noradrenaline release near the cardiac layers may increase the contraction rate of the tissue.

Figure 5A:
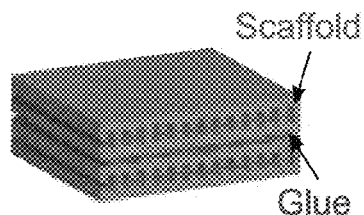
Figure 5B:
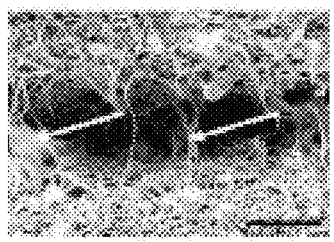
Figure 5C:
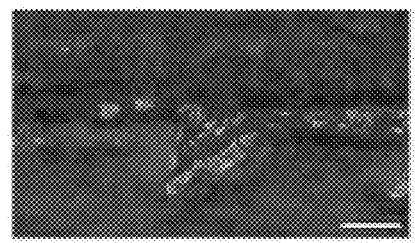
Figure 5D:
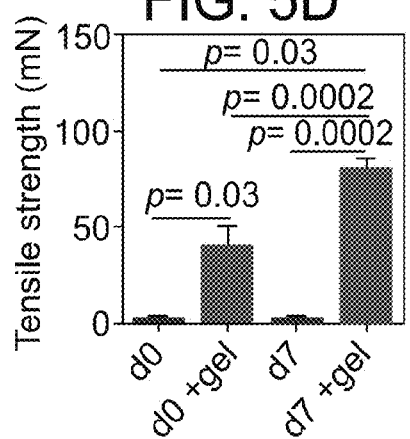

After engineering the distinct tissue layers, the present inventors next sought to integrate them to form a thick modular tissue. A thermoresponsive ECM-based hydrogel which solidifies at 37° C. was used as a biological glue for layer integration. Thin layers of the glue were deposited between the tissue layers, and the assembled patch was heated to 37° C. in an incubator. The integration was then assessed by SEM, histology and immunostaining (FIGS. 5B, 5C and 5D and FIGS. 11B-C). Although the ECM hydrogel was able to glue the layers, these were not tightly packed, allowing for nutrients and oxygen diffusion. Next, the binding force between the different layers was assessed (FIG. 5D). As shown by the tensile strength measurements, immediately after integration, the force needed to separate the glued layers was significantly higher than the force needed to separate non-glued layers (p=0.03). More importantly, the binding force between the ECM-glued layers was sufficiently strong to withstand manual manipulation and surgical suturing to the host. Further culturing the integrated layers for 7 days significantly strengthened their adherence (p=0.03), possibly by additional secretion of ECM proteins by the cells.

Figure 5E:
Figure 11A:
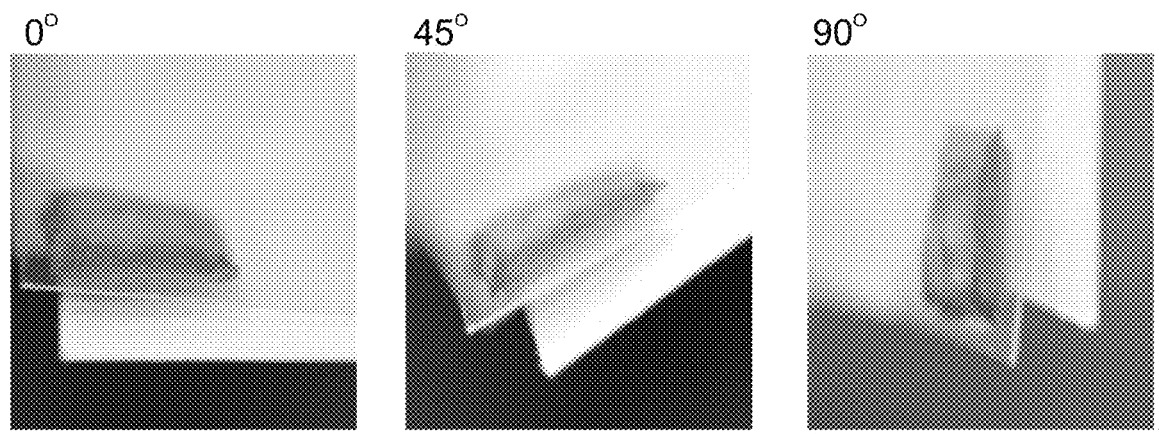
Figure 11B:
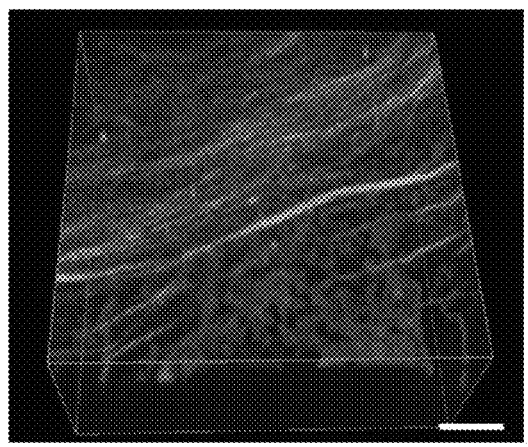
Figure 11C:
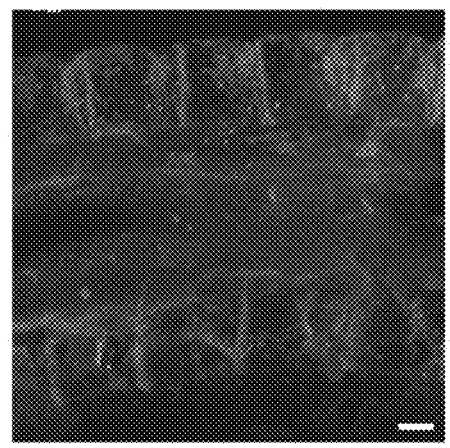
Figure 11D:
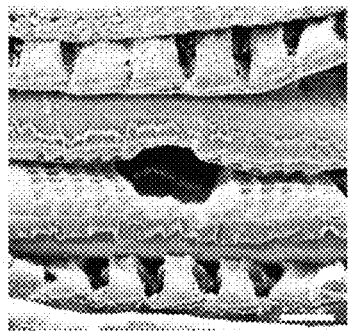
Figure 11E:
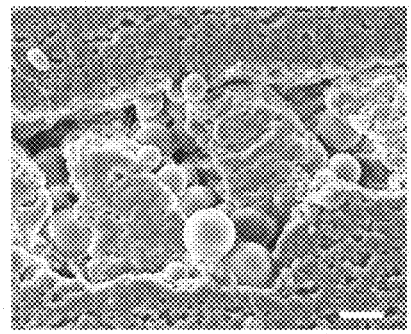

As cardiac tissues and blood vessels may need different assembly conditions (including cultivation periods, growth factors and supporting matrices), 7-day cardiac layers and 3-day endothelial cell layers were integrated together with the controlled release layers to form a mm thick cardiac patch. The engineered tissue was composed of 6 cardiac layers, 6 endothelial cell layers with VEGF particles and 2 DEX-releasing microparticles layers (FIG. 5E). To create the closed lumens two layers of vasculature were simply glued on top of each other and incorporated in-between two cardiac tissue layers (FIGS. 6 and 11D). The DEX layers were integrated to both ends of the construct to affect the patch's surroundings (FIG. 11E).

Figure 5F:

As the native myocardium has tight connections in all directions, the present inventors next sought to additionally evaluate the electrical coupling in the z-direction, between the different cardiac layers. Prior to cardiac cell seeding, thin metal electrodes were deposited on an electrospun fiber scaffold, enabling local electrical stimulation of the cells within. Then, 5 cardiac tissue layers were stacked on this electrode-containing layer to create the thick patch with an upper cardiac layer that was pre-treated with calcium dye. Next, electrical stimuli (1 or 2 Hz) were applied to the bottom layer and the corresponding calcium wave fronts were recorded from the upper layer, indicating on electrical integration within the z-direction (FIG. 5F).

Figure 5G:
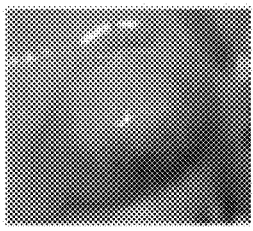
Figure 5H:
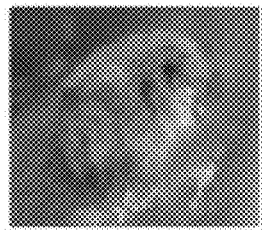
Figure 5I:
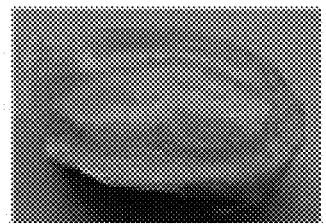
Figure 5J:
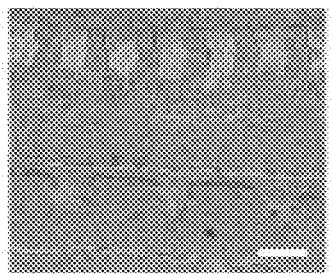
Figure 5K:
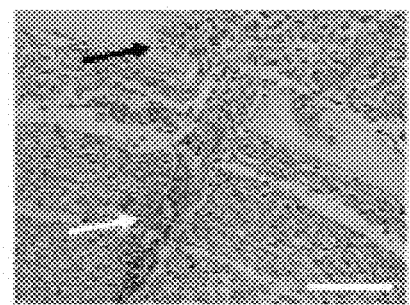
Figure 5L:
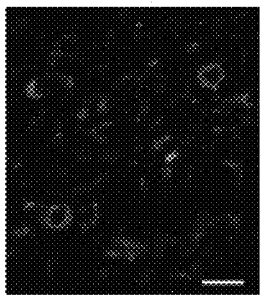
Figure 5M:
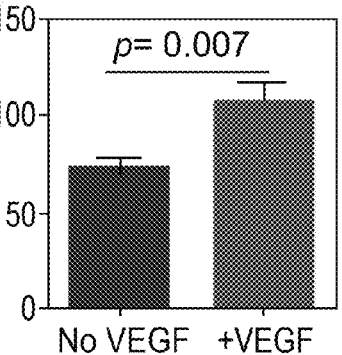
Figure 5N:
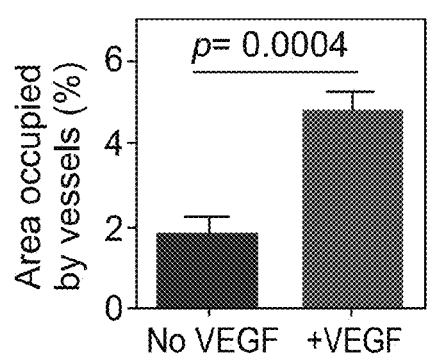
Figure 11F:
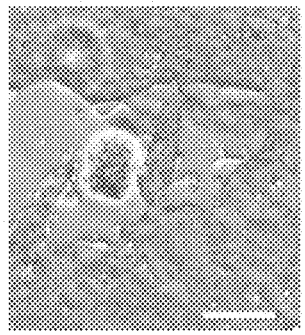

Finally, the ability of the modular cardiac patch to promote vascularization in-vivo was assessed. Cellular patches with or without VEGF-releasing microparticles were subcutaneously transplanted in rats for 2 weeks before they were sacrificed. A macroscopic view of the patches in the animals suggested that while the patches without the VEGF remained white, the VEGF loaded patches were filled with blood vessels as judged by their red color (FIGS. 5G and 5H). Cross sectioning the patches revealed that the structure of the layers was maintained (FIGS. 5I and 5J). Furthermore, VEGF microparticles could be seen on the blood vessel layer, suggesting that although the particles have started to degrade and release their content, some of them were still intact within their mesh (FIG. 11F). Histological analysis and Immunostaining the extracts for smooth muscle cells, which stabilize blood vessels, revealed that the release of VEGF encouraged infiltration of blood vessels into the patch and its surroundings (FIGS. 5K and 5L and FIGS. 12A-B). Moreover, red blood cells within the host blood vessels were seen entering into the core of the patch and into its channels, indicating anastomosis between the host vasculature and the engineered tissue (FIG. 5K). Quantification of blood vessels within the engineered patch revealed significantly higher number of vessels per $mm^2$ tissue (FIG. 5M; p=0.007) in the patch containing VEGF releasing particles, as compared to the pristine scaffolds. Moreover, the percent of the total area of blood vessels within the VEGF-releasing patch was significantly higher (FIG. 5N; p=0.0004). Taken together, these results indicate that the VEGF microparticulate layer can improve blood vessel infiltration into the cardiac patch.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Fleischer S & Dvir T (2013) Tissue engineering on the nanoscale: lessons from the heart. *Current opinion in biotechnology* 24(4):664-671.
2. Dvir T, Timko B P, Kohane D S, & Langer R (2011) Nanotechnological strategies for engineering complex tissues. *Nature nanotechnology* 6(1):13-22.
3. Ogle B M, et al. (2016) Distilling complexity to advance cardiac tissue engineering. *Science Translational Medicine* 8(342):342ps313-342ps313.
4. Pope A J, Sands G B, Smaill B H, & LeGrice I J (2008) Three-dimensional transmural organization of perimysial collagen in the heart. *American Journal of Physiology-Heart and Circulatory Physiology* 295(3):H1243-H1252.
5. LeGrice I J, et al. (1995) Laminar structure of the heart: ventricular myocyte arrangement and connective tissue architecture in the dog. *American Journal of Physiology-Heart and Circulatory Physiology* 269(2):H571-H582.
6. Corno A F, Kocica M J, & Torrent-Guasp F (2006) The helical ventricular myocardial band of Torrent-Guasp: potential implications in congenital heart defects. *European journal of cardio-thoracic surgery* 29(Supplement 1):S61-S68.
7. Engelmayr G C, et al. (2008) Accordion-like honeycombs for tissue engineering of cardiac anisotropy. *Nature materials* 7(12):1003-1010.
8. Kim D-H, et al. (2010) Nanoscale cues regulate the structure and function of macroscopic cardiac tissue constructs. *Proceedings of the National Academy of Sciences* 107(2):565-570.
9. Fleischer S, et al. (2013) Spring-like fibers for cardiac tissue engineering. *Biomaterials* 34(34):8599-8606.
10. Fleischer S, Shevach M, Feiner R, & Dvir T (2014) Coiled fiber scaffolds embedded with gold nanoparticles improve the performance of engineered cardiac tissues. *Nanoscale* 6(16):9410-9414.
11. Feinberg A W, et al. (2012) Controlling the contractile strength of engineered cardiac muscle by hierarchal tissue architecture. *Biomaterials* 33(23):5732-5741.
12. Feinberg A W, et al. (2007) Muscular thin films for building actuators and powering devices. *Science* 317 (5843): 1366-1370.
13. Ruvinov E & Cohen S (2016) Alginate biomaterial for the treatment of myocardial infarction: progress, translational strategies, and clinical outlook: from ocean algae to patient bedside. *Advanced drug delivery reviews* 96:54-76.
14. Shevach M, Soffer-Tsur N, Fleischer S, Shapira A, & Dvir T (2014) Fabrication of omentum-based matrix for engineering vascularized cardiac tissues. *Biofabrication* 6(2):024101.
15. Shevach M, et al. (2015) Omentum ECM-based hydrogel as a platform for cardiac cell delivery. *Biomedical Materials* 10(3):034106.
16. Shevach M, Fleischer S, Shapira A, & Dvir T (2014) Gold nanoparticle-decellularized matrix hybrids for cardiac tissue engineering. *Nano letters* 14(10):5792-5796.
17. Vunjak-Novakovic G, et al. (2009) Challenges in cardiac tissue engineering. *Tissue Engineering Part B: Reviews* 16(2): 169-187.
18. Zhang Y S, et al. (2016) Bioprinting 3D Microfibrous Scaffolds for Engineering Endothelialized Myocardium and Heart-on-a-Chip. *Biomaterials*.
19. Kolewe M E, et al. (2013) 3D structural patterns in scalable, elastomeric scaffolds guide engineered tissue architecture. *Advanced Materials* 25(32):4459-4465.
20. Ye X, et al. (2014) Scalable units for building cardiac tissue. *Advanced Materials* 26(42):7202-7208.
21. Zhang B, et al. (2016) Biodegradable scaffold with built-in vasculature for organ-on-a-chip engineering and direct surgical anastomosis. *Nature materials*.
22. Shin M, Ishii O, Sueda T, & Vacanti J (2004) Contractile cardiac grafts using a novel nanofibrous mesh. *Biomaterials* 25(17):3717-3723.
23. Fleischer S, Miller J, Hurowitz H, Shapira A, & Dvir T (2015) Effect of fiber diameter on the assembly of functional 3D cardiac patches. *Nanotechnology* 26(29): 291002.
24. Fleischer S, et al. (2014) Albumin fiber scaffolds for engineering functional cardiac tissues. *Biotechnology and bioengineering* 111(6): 1246-1257.
25. Weis S M, et al. (2000) Myocardial mechanics and collagen structure in the osteogenesis imperfecta murine (oim). *Circulation Research* 87(8):663-669.
26. Omens J H (1998) Stress and strain as regulators of myocardial growth. *Progress in biophysics and molecular biology* 69(2):559-572.
27. Coirault C, et al. (1998) Increased compliance in diaphragm muscle of the cardiomyopathic Syrian hamster. *Journal of Applied Physiology* 85(5):1762-1769.
28. Parsa H, Ronaldson K, & Vunjak-Novakovic G (2016) Bioengineering methods for myocardial regeneration. *Advanced drug delivery reviews* 96:195-202.
29. Sapir Y, Cohen S, Friedman G, & Polyak B (2012) The promotion of in vitro vessel-like organization of endothelial cells in magnetically responsive alginate scaffolds. *Biomaterials* 33(16):4100-4109.

30. Dvir T, Benishti N, Shachar M, & Cohen S (2006) A novel perfusion bioreactor providing a homogenous milieu for tissue regeneration. *Tissue engineering* 12(10): 2843-2852.
31. Radisic M, Marsano A, Maidhof R, Wang Y, & Vunjak-Novakovic G (2008) Cardiac tissue engineering using perfusion bioreactor systems. *Nature protocols* 3(4):719-738.
32. Montgomery M, Zhang B, & Radisic M (2014) Cardiac Tissue Vascularization From Angiogenesis to Microfluidic Blood Vessels. *Journal of cardiovascular pharmacology and therapeutics:*1074248414528576.
33. Caspi O, et al. (2007) Tissue engineering of vascularized cardiac muscle from human embryonic stem cells. *Circulation Research* 100(2):263-272.
34. Lesman A, et al. (2009) Transplantation of a tissue-engineered human vascularized cardiac muscle. *Tissue Engineering Part A* 16(1):115-125.
35. Marsano A, et al. (2013) The effect of controlled expression of VEGF by transduced myoblasts in a cardiac patch on vascularization in a mouse model of myocardial infarction. *Biomaterials* 34(2):393-401.
36. Freeman I & Cohen S (2009) The influence of the sequential delivery of angiogenic factors from affinity-binding alginate scaffolds on vascularization. *Biomaterials* 30(11):2122-2131.
37. Dvir T, et al. (2009) Prevascularization of cardiac patch on the omentum improves its therapeutic outcome. *Proceedings of the National Academy of Sciences* 106(35): 14990-14995.
38. Vishwakarma A, et al. (2016) Engineering Immunomodulatory Biomaterials To Tune the Inflammatory Response. *Trends in biotechnology* 34(6):470-482.
39. Feiner R, et al. (2016) Engineered hybrid cardiac patches with multifunctional electronics for online monitoring and regulation of tissue function. *Nature materials*.

What is claimed:

1. A scaffold for tissue engineering comprising at least two layers, wherein each of said at least two layers are fabricated from a composition of matter which comprises a plurality of electrospun albumin fibers, wherein an outer surface of the composition comprises a pattern of ridges or indentations, wherein the width of an individual ridge or indentation of said pattern of ridges or indentations is wider than the diameter of a single electrospun albumin fiber of said plurality of electrospun albumin fibers, each layer comprising a pattern with distinct indentations or ridges.

2. The scaffold of claim 1, wherein at least one of the layers is seeded with cells.

3. The scaffold of claim 2, wherein said cells are selected from the group consisting of cardiomyocytes, endothelial cells, pancreatic beta cells, hepatocytes, skin cells, lung cells and skeletal muscle cells.

4. The scaffold of claim 2, wherein a first of said at least two layers is seeded with cardiomyocytes and a second of said at least two layers is seeded with endothelial cells.

5. The scaffold of claim 1, wherein a first of said at least two layers comprises a pattern of grooves and a second of said at least two layers comprises a pattern of grooves and cages.

6. The scaffold of claim 5, wherein said cages are loaded with particles comprising an agent selected from the group consisting of a growth promoting agent, a differentiating agent, a neurotransmitter, a pro-angiogenic agent, an anti-inflammatory agent and a drug.

7. The scaffold of claim 1, comprising at least three layers, wherein the third layer is patterned with cages loaded with particles comprising an agent selected from the group consisting of a growth promoting agent, a neurotransmitter, a differentiating agent, a pro-angiogenic agent, an anti-inflammatory agent and a drug.

8. The scaffold of claim 1, wherein said at least two layers are adhered to one another using a biological glue.

* * * * *